United States Patent
Bettles et al.

(10) Patent No.: US 10,363,330 B2
(45) Date of Patent: *Jul. 30, 2019

(54) ELECTRONIC GADGET DISINFECTION

(71) Applicant: Sensor Electronic Technology, Inc., Columbia, SC (US)

(72) Inventors: Timothy James Bettles, Irmo, SC (US); Yuri Bilenko, Columbia, SC (US); Saulius Smetona, Concord, NC (US); Alexander Dobrinsky, Silver Spring, MD (US); Michael Shur, Vienna, VA (US); Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/856,891

(22) Filed: Dec. 28, 2017

(65) Prior Publication Data

US 2018/0117201 A1    May 3, 2018

Related U.S. Application Data

(63) Continuation of application No. 14/853,105, filed on Sep. 14, 2015, now Pat. No. 9,974,877, and a (Continued)

(51) Int. Cl.
*A61L 2/10* (2006.01)
*A61L 2/24* (2006.01)

(52) U.S. Cl.
CPC .. *A61L 2/24* (2013.01); *A61L 2/10* (2013.01)

(58) Field of Classification Search
CPC .................................... A61L 2/10; A61L 2/24
See application file for complete search history.

(56) References Cited

U.S. PATENT DOCUMENTS

| 4,806,770 A | 2/1989 | Hylton et al. |
| 6,239,442 B1 | 5/2001 | Iimura |

(Continued)

FOREIGN PATENT DOCUMENTS

| CN | 201752504 | 3/2011 |
| KR | 20120041518 | 5/2012 |
| WO | 2008096123 | 8/2008 |

OTHER PUBLICATIONS

"Spectroline—CB-4000A—CellBlaster: UV Cell Phone Sanitizer—Operator's Manual," Sep. 2013, 26 pages.
(Continued)

*Primary Examiner* — Eliza W Osenbaugh-Stewart
(74) *Attorney, Agent, or Firm* — LaBatt, LLC

(57) ABSTRACT

A solution for disinfecting electronic devices is provided. An ultraviolet radiation source is embedded within an ultraviolet absorbent case. While the electronic device is within the ultraviolet absorbent case, ultraviolent radiation is directed at the electronic device. A monitoring and control system monitors a plurality of attributes for the electronic device, which can include: a frequency of usage for the device, a biological activity at a surface of the device, and a disinfection schedule history for the device. Furthermore, the monitoring and control system can detect whether the device is being used. Based on the monitoring, the monitoring and control system controls the ultraviolet radiation directed at the electronic device.

20 Claims, 16 Drawing Sheets

Related U.S. Application Data continuation-in-part of application No. 14/144,053, filed on Dec. 30, 2013, now Pat. No. 9,138,499.

(60) Provisional application No. 62/050,126, filed on Sep. 13, 2014, provisional application No. 61/747,640, filed on Dec. 31, 2012, provisional application No. 61/753,997, filed on Jan. 18, 2013, provisional application No. 61/771,016, filed on Feb. 28, 2013.

(56) References Cited

U.S. PATENT DOCUMENTS

| | | | |
|---|---|---|---|
| 6,278,122 | B1 | 8/2001 | Gagnon |
| 6,458,331 | B1 | 10/2002 | Roberts |
| 6,605,260 | B1 | 8/2003 | Busted |
| 6,923,367 | B1 | 8/2005 | Grossman et al. |
| 7,372,044 | B2 | 5/2008 | Ross |
| 7,553,456 | B2 | 6/2009 | Gaska et al. |
| 7,634,996 | B2 | 12/2009 | Gaska et al. |
| 8,203,124 | B2 | 6/2012 | Havens et al. |
| 8,277,734 | B2 | 10/2012 | Koudymov et al. |
| 8,318,089 | B2 | 11/2012 | Brown-Skrobot et al. |
| 8,330,121 | B2 | 12/2012 | Douglas |
| 8,334,521 | B2 | 12/2012 | Deshays |
| 8,431,910 | B1 | 4/2013 | Perry |
| 8,481,970 | B2 | 7/2013 | Cooper et al. |
| 8,980,178 | B2 | 3/2015 | Gaska et al. |
| 9,034,271 | B2 | 5/2015 | Shur et al. |
| 9,061,082 | B2 | 6/2015 | Gaska et al. |
| 9,138,499 | B2 | 9/2015 | Bettles et al. |
| 9,179,703 | B2 | 11/2015 | Shur et al. |
| 9,572,903 | B2 | 2/2017 | Dobrinsky et al. |
| 9,603,960 | B2 | 3/2017 | Dobrinsky et al. |
| 9,687,577 | B2 | 6/2017 | Dobrinsky et al. |
| 9,707,307 | B2 | 7/2017 | Shur et al. |
| 9,718,706 | B2 | 8/2017 | Smetona et al. |
| 9,724,441 | B2 | 8/2017 | Shur et al. |
| 9,750,830 | B2 | 9/2017 | Shur et al. |
| 9,757,486 | B2 | 9/2017 | Dobrinsky et al. |
| 9,795,699 | B2 | 10/2017 | Shur et al. |
| 9,801,965 | B2 | 10/2017 | Bettles et al. |
| 9,802,840 | B2 | 10/2017 | Shturm et al. |
| 2007/0057197 | A1 | 3/2007 | Chor |
| 2008/0067417 | A1 | 3/2008 | Lane et al. |
| 2008/0199353 | A1 | 8/2008 | Mlodzinski et al. |
| 2009/0206674 | A1 | 8/2009 | Noguchi et al. |
| 2009/0280035 | A1 | 11/2009 | Koudymov et al. |
| 2010/0044582 | A1 | 2/2010 | Cooper et al. |
| 2011/0291995 | A1 | 12/2011 | Shr et al. |
| 2013/0001435 | A1 | 1/2013 | Engelhardt et al. |
| 2013/0048545 | A1 | 2/2013 | Shatalov et al. |
| 2013/0048876 | A1 | 2/2013 | Crawford |
| 2013/0256560 | A1 | 10/2013 | Yerby |
| 2014/0060104 | A1 | 3/2014 | Shur et al. |
| 2014/0183377 | A1 | 7/2014 | Bettles et al. |
| 2014/0202962 | A1 | 7/2014 | Bilenko et al. |
| 2014/0264070 | A1 | 9/2014 | Bettles et al. |
| 2014/0264075 | A1 | 9/2014 | LaPorte et al. |
| 2014/0264076 | A1 | 9/2014 | Bettles et al. |
| 2014/0341777 | A1 | 11/2014 | Deshays et al. |
| 2015/0165079 | A1 | 6/2015 | Shur et al. |
| 2015/0297767 | A1 | 10/2015 | Gaska et al. |
| 2015/0336810 | A1 | 11/2015 | Smetona et al. |
| 2016/0000953 | A1 | 1/2016 | Bettles et al. |
| 2016/0114186 | A1 | 4/2016 | Dobrinsky et al. |
| 2016/0324996 | A1 | 11/2016 | Bilenko et al. |
| 2017/0057842 | A1 | 3/2017 | Dobrinsky et al. |
| 2017/0100494 | A1 | 4/2017 | Dobrinsky et al. |
| 2017/0100495 | A1 | 4/2017 | Shur et al. |
| 2017/0100496 | A1 | 4/2017 | Shur et al. |
| 2017/0189711 | A1 | 7/2017 | Shur et al. |
| 2017/0245527 | A1 | 8/2017 | Dobrinsky et al. |
| 2017/0245616 | A1 | 8/2017 | Lakios et al. |
| 2017/0281812 | A1 | 10/2017 | Dobrinsky et al. |
| 2017/0368215 | A1 | 12/2017 | Shatalov et al. |
| 2018/0117194 | A1 | 5/2018 | Dobrinsky et al. |

OTHER PUBLICATIONS

"UV Light Sterilizer Cell Phone iPode iPhone ear bud Sanitizer—Keeps Electronic Devices Germ Free!" http://www.ankaka.com/uv-light-sterilizer-cell-phone-ipod-iphone-ear-bud-sanitizer-keeps-electronic-devices-germ-free_p48896.html. Accessed Dec. 17, 2013, 5 pages.

"Portable UV Sterilizer for iPhone/iPod." http://www.sinco-elec.com/e_products/Portable-UV-Sterilizer-for-iPhoneiPod-p126.html. Accessed Dec. 17, 2013, 2 pages.

Osenbaugh-Stewart, E., U.S. Appl. No. 14/853,105, Final Office Action2, dated Oct. 23, 2016, 19 pages.

Osenbaugh-Stewart, E., U.S. Appl. No. 14/853,105, Non-Final Office Action2, dated May 17, 2017, 19 pages.

Osenbaugh-Stewart, E., U.S. Appl. No. 14/853,105, Final Office Action, dated Oct. 19, 2016, 16 pages.

Osenbaugh-Stewart, E., U.S. Appl. No. 14/853,105, Office Action, dated May 6, 2016, 23 pages.

Vanore, D., U.S. Appl. No. 14/144,053, Notice of Allowance, dated May 20, 2015, 5 pages.

Vanore, D., U.S. Appl. No. 14/144,053, Office Action, dated Jan. 26, 2015, 11 pages.

Kim, PCT Search Report for PCT Application No. US2013/078336, dated Apr. 1, 2014, 11 pages.

Osenbaugh-Stewart, E., U.S. Appl. No. 14/853,105, Notice of Allowance, dated Jan. 19, 2018, 8 pages.

Osenbaugh-Stewart, E., U.S. Appl. No. 15/986,684, Office Action 1, dated Mar. 29, 2019, 19 pages.

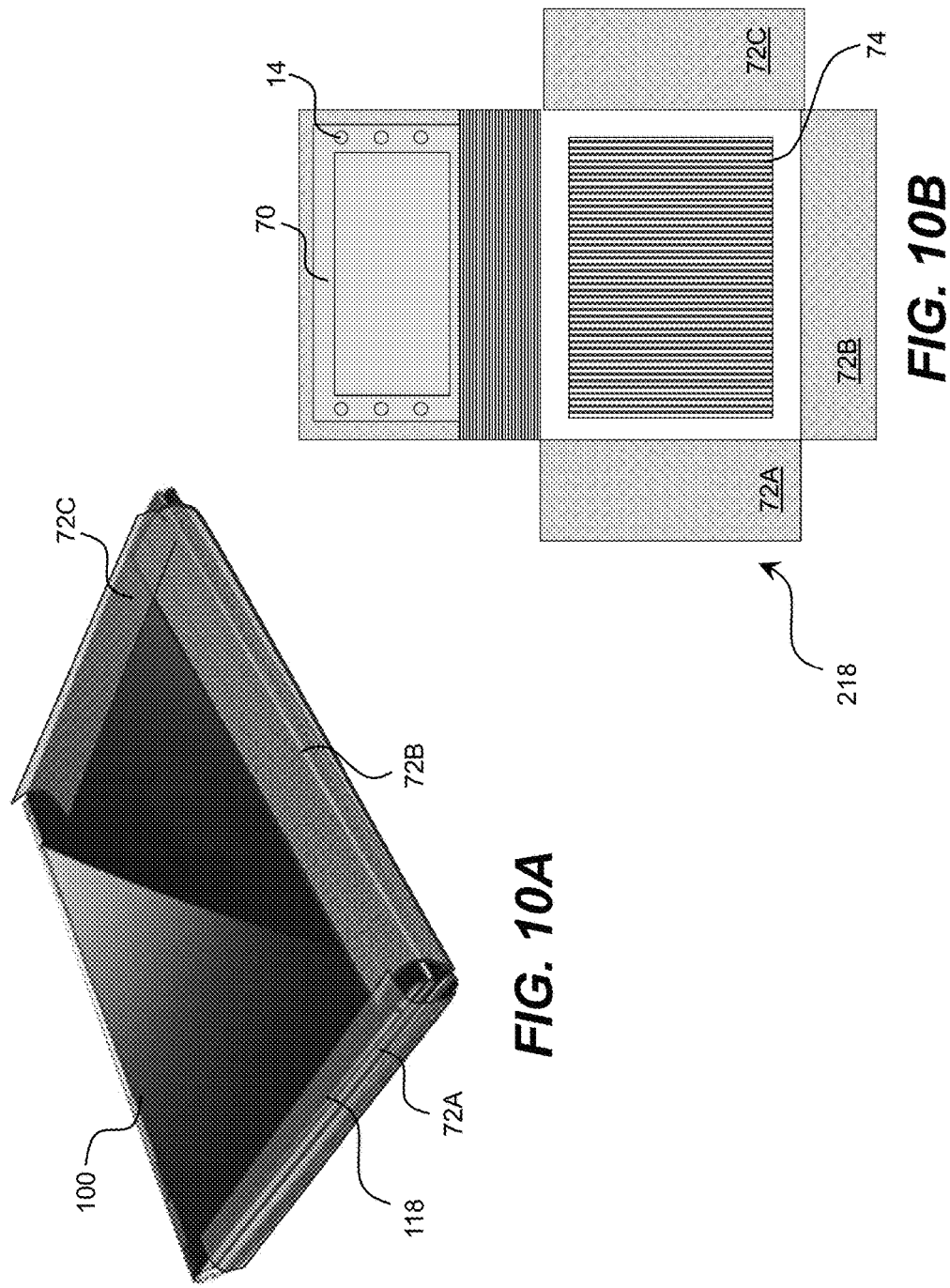

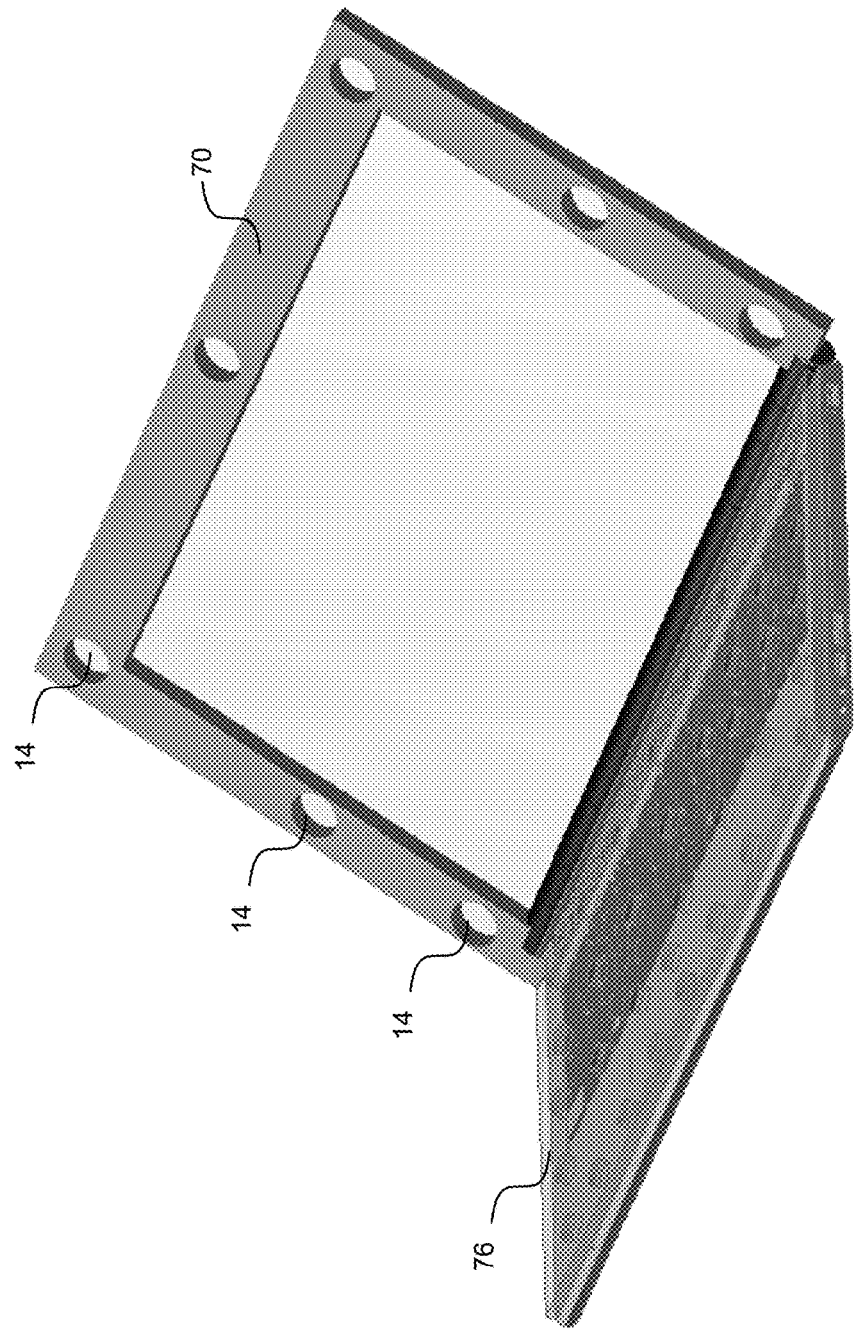

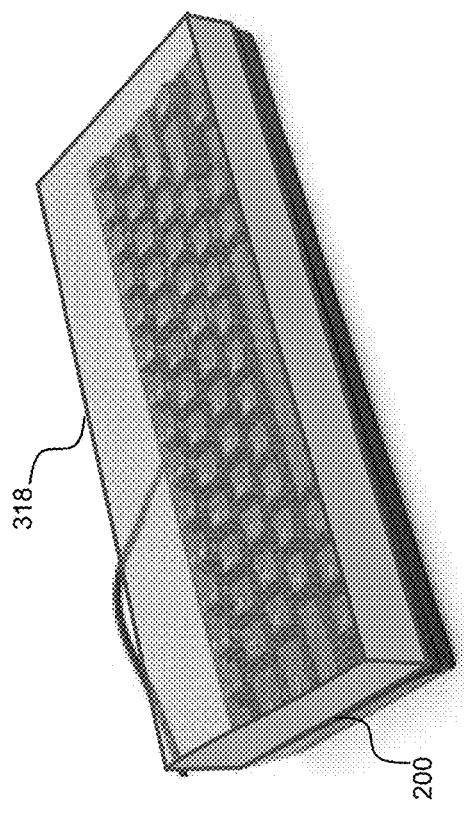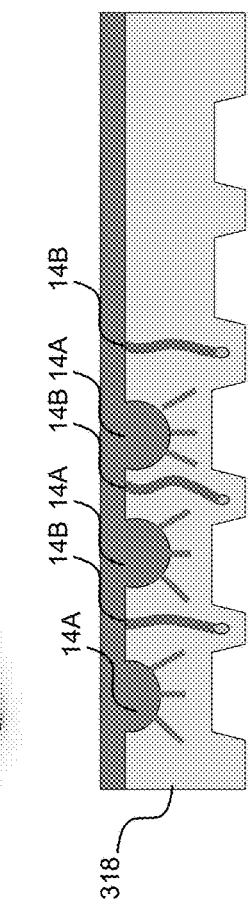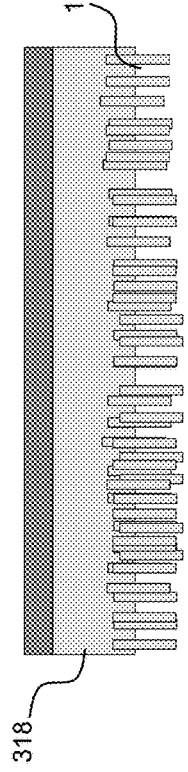

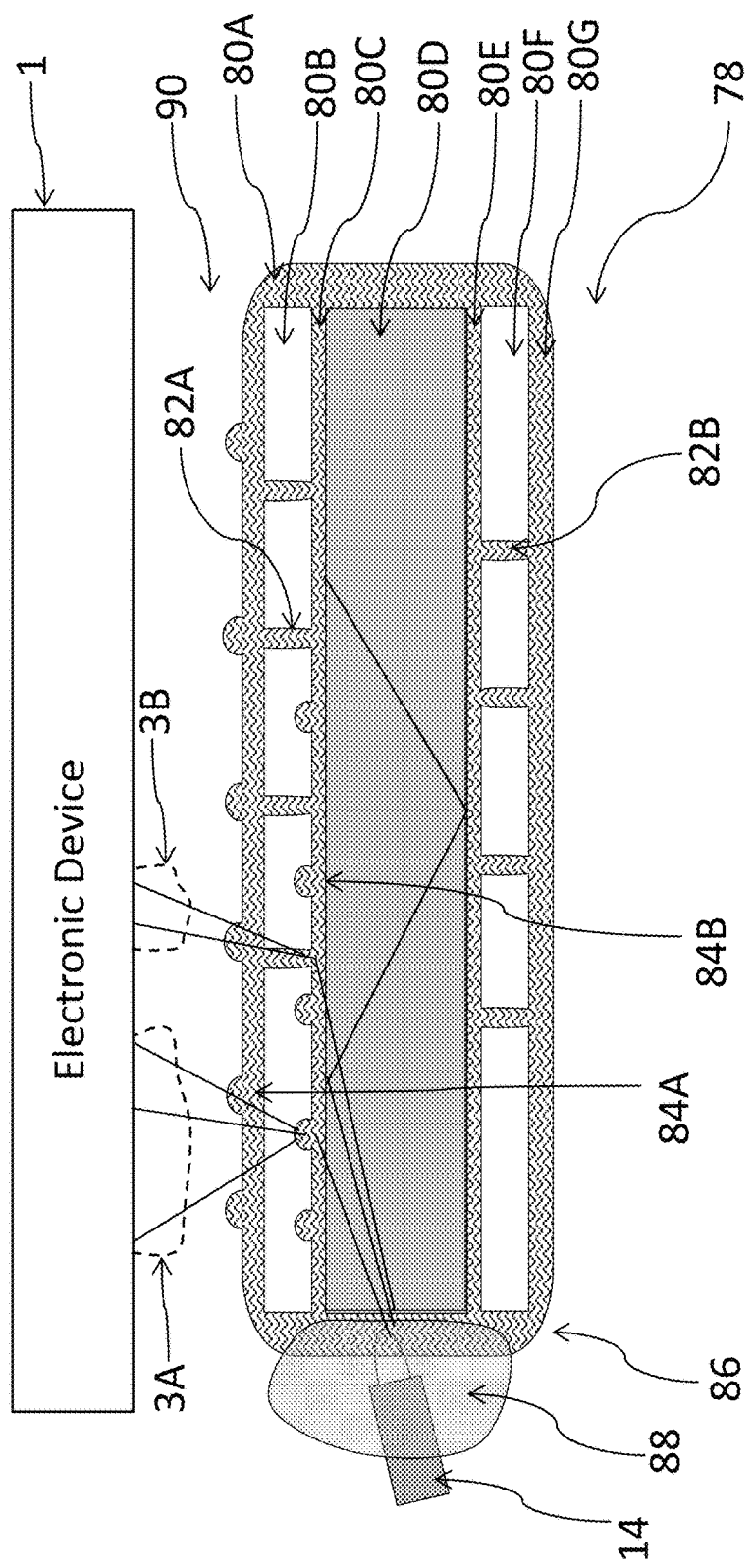

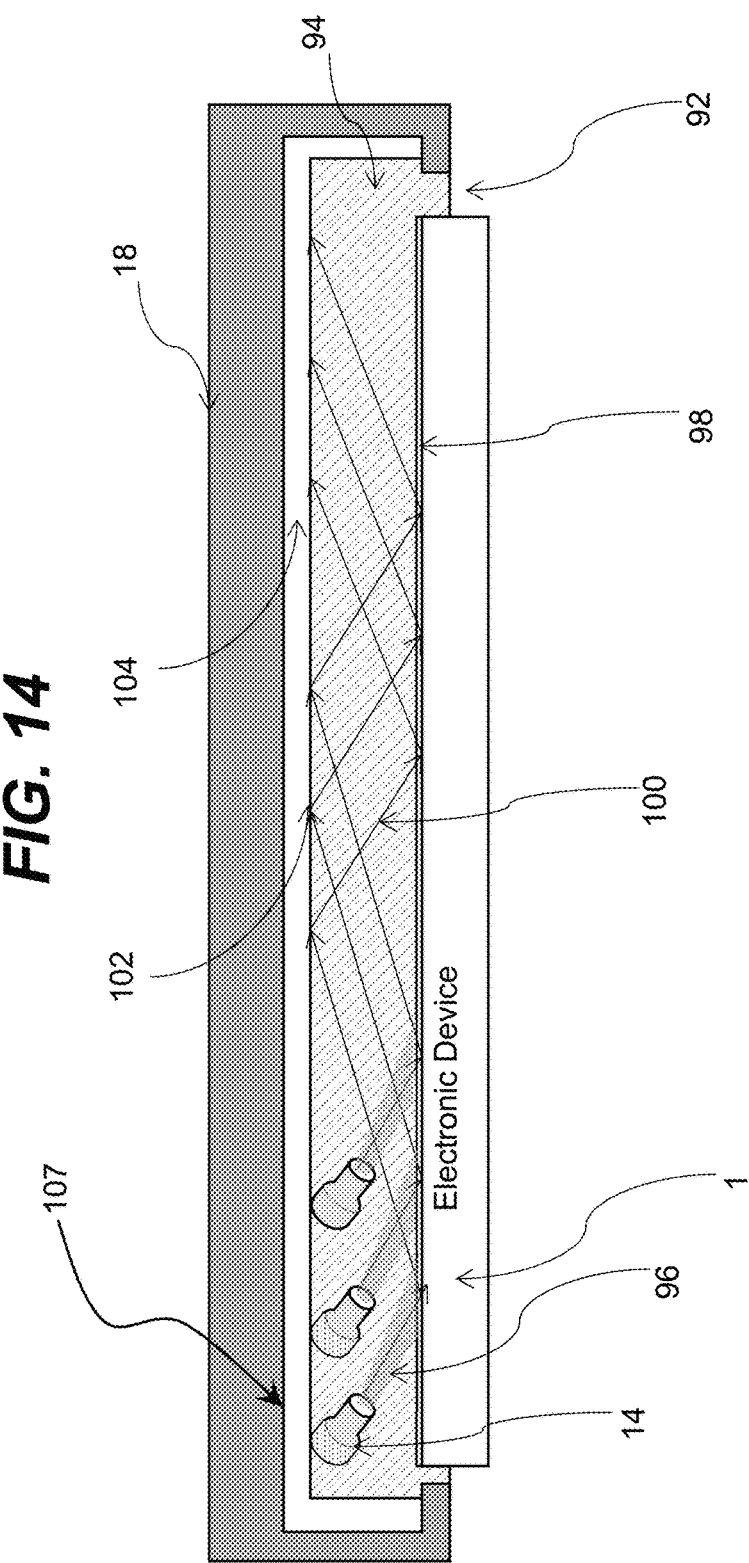

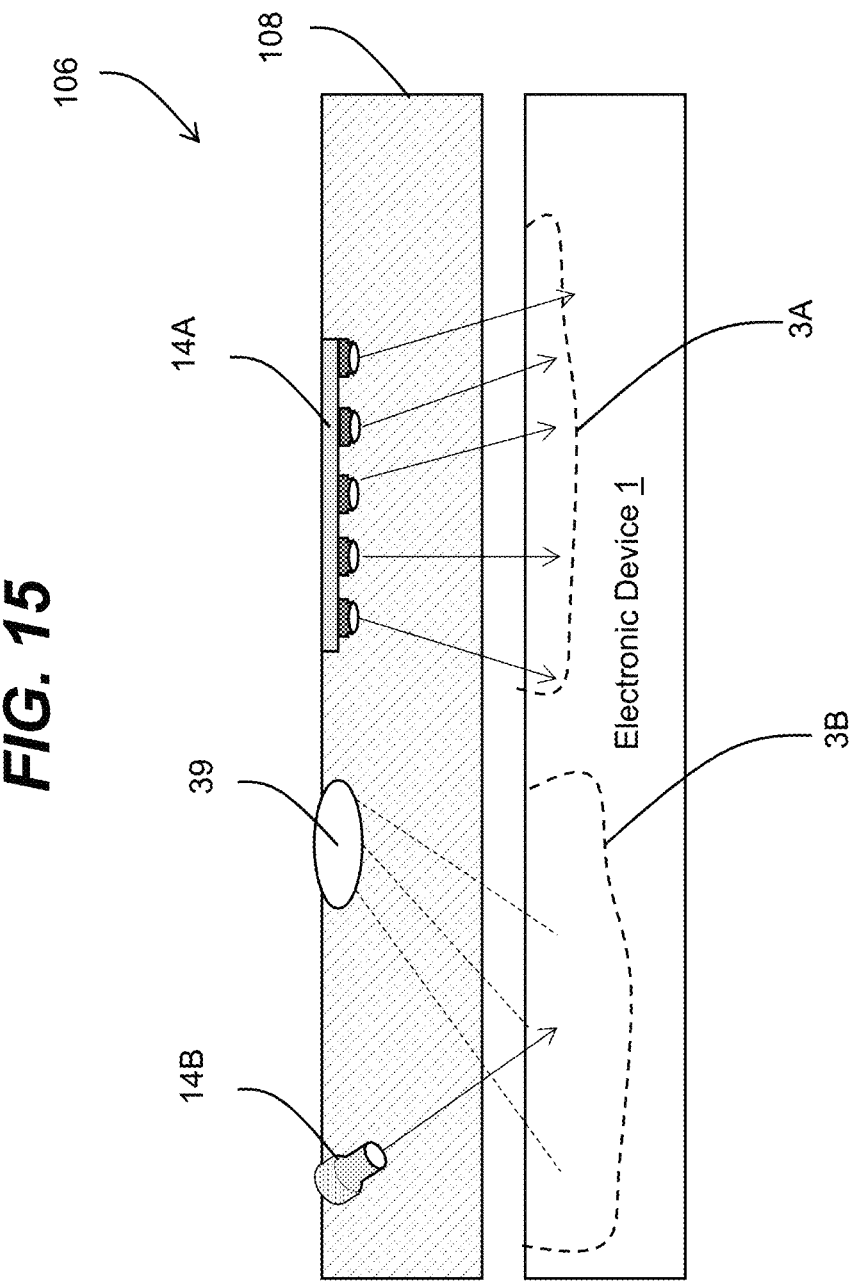

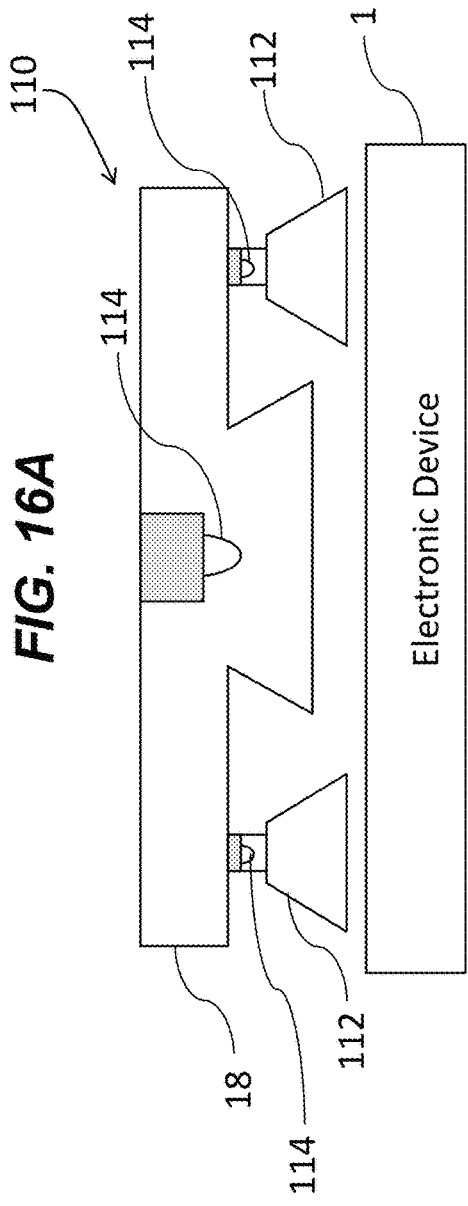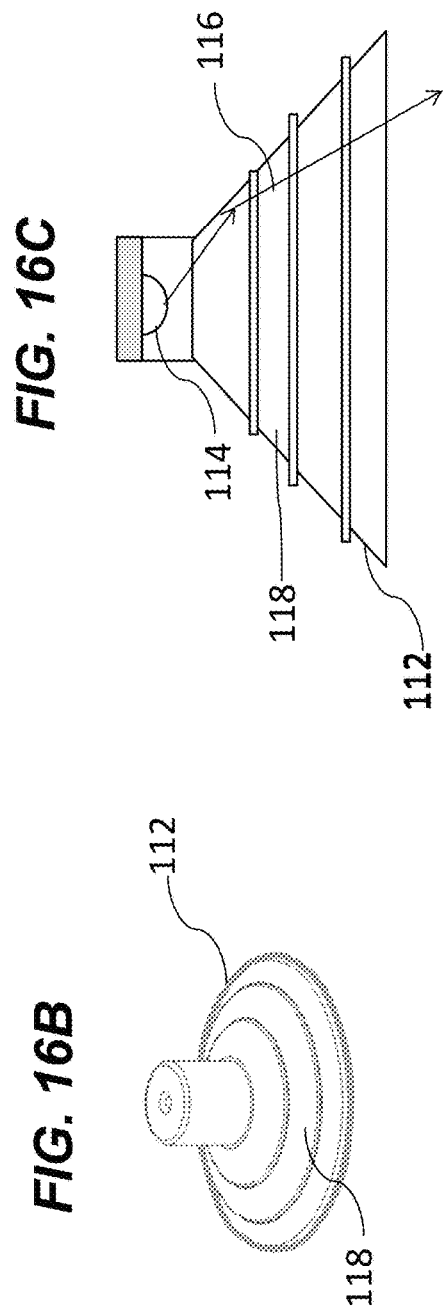

ELECTRONIC GADGET DISINFECTION

REFERENCE TO RELATED APPLICATION

The present patent application is a continuation of U.S. application Ser. No. 14/853,105, filed on 14 Sep. 2015, which claims the benefit of U.S. Provisional Application No. 62/050,126, filed on 13 Sep. 2014, and which is a continuation-in-part application of U.S. application Ser. No. 14/144,053, filed on 30 Dec. 2013, which claims the benefit of U.S. Provisional Application No. 61/747,640, filed on 31 Dec. 2012; U.S. Provisional Application No. 61/753,997, filed on 18 Jan. 2013; and U.S. Provisional Application No. 61/771,016, filed on 28 Feb. 2013, all of which are hereby incorporated by reference in its entirety.

TECHNICAL FIELD

The disclosure relates generally to ultraviolet radiation, and more particularly, to a solution for disinfecting an electronic gadget using ultraviolet radiation.

BACKGROUND ART

Ultraviolet (UV) radiation has been utilized to sanitize different devices. For example, there is an approach for sanitizing toothbrushes using UV light. The apparatus relies on a UV lamp of low intensity for emitting UV radiation in the 200 to 300 nanometer wavelength range, as well as some radiation in the visible range above 300 nanometers and in the ozone producing range below 200 nanometers.

Other sanitizing devices are also known in the art. For example, one approach proposes a mailbox enclosure to sanitize mail articles with UV light and other means. Another approach proposes a surgical tool sterilizing enclosure that utilizes UV light as well as chemical and other sanitizing agents.

Other approaches include a computer input device sterilization apparatus including UV sterilization in an enclosed container to kill bacteria and other disease carrying organisms. The approach includes a horizontal or vertical container dimensioned to fit over computer input devices such as keyboards, mice, trackballs, touchpads and the like. A UV source within the container irradiates the computer input device with UV light which generates ozone gas, thereby killing any microorganisms that might reside on the computer input devices. UV radiation below 200 nm can also be used to create ozone gas having germicidal characteristics. The ozone gas is circulated in and around the input device(s) to provide further sterilization with the UV radiation. A sterilization switch turns the UV source off when the container is opened. A timer/power circuit provides the timed application of power to the UV lamps to provide UV illumination consistent with the substantial sterilization of the input device in question.

There are currently also UV devices available to sterilize mobile phones, such as the UV Sterilizer for the iPhone® from Sinco-Electronic Gifts Co. The UV Sterilizer is a desktop unit. A user places his/her phone into the sterilizer for approximately five minutes. The device turns a blue light emitting diode (LED) on to indicate the start of the sterilization process. Once the blue LED turns of, the sterilization process is complete. Such devices typically utilize mercury lamps to generate the ultraviolet light.

SUMMARY OF THE INVENTION

In view of the prior art, the inventors have identified various challenges and limitations of current approaches for disinfecting electronic devices. For example, the inventors have noted that current approaches do not utilize low voltage UV LEDs for disinfecting devices and are not portable. Additionally, current sterilization devices cannot be used as part of the electronic device case without endangering the user.

Embodiments provide a solution including improved UV LED disinfection of electronic devices. For example, an embodiment can utilize UV LEDs, as low operating voltage semiconductor devices, for safe and radio frequency (RF) interference free disinfection. In an illustrative embodiment, the disinfection device can be used as a part of a case for storing the electronic device without harming the user or the electronic device. Furthermore, since the disinfection device is a part of the electronic device case, the user can use the disinfection device at any time. Additionally, in an embodiment, the UV light emitted by the UV LEDs is recycled to provide for more efficient disinfection.

Aspects of the invention provide a solution for disinfecting electronic devices using ultraviolet radiation. An ultraviolet radiation source is embedded within an ultraviolet absorbent case. While the electronic device is within the ultraviolent absorbent case, ultraviolent radiation is generated and directed at the electronic device. A monitoring and control system monitors a plurality of attributes for the electronic device, which can include: a frequency of usage for the device, a biological activity at a surface of the device, and a disinfection schedule history for the device. Furthermore, the monitoring and control system can detect whether the device is being used. Based on the monitoring, the monitoring and control system controls the ultraviolet radiation directed at the electronic device.

A first aspect of the invention provides a system comprising: an ultraviolet absorbent enclosure for containing at least one part of an electronic device; at least one ultraviolet radiation source embedded within the ultraviolet absorbent enclosure, the at least one ultraviolet radiation source configured to generate ultraviolet radiation directed at the part of the electronic device; and a monitoring and control system for managing the ultraviolet radiation directed at the part of the electronic device by performing a method comprising: monitoring the electronic device for at least one of: a frequency of usage of the electronic device, a presence of biological activity on the electronic device and a disinfection schedule history for the electronic device; and controlling, based on the monitoring, the ultraviolet radiation directed at the part of the electronic device.

A second aspect of the invention provides an apparatus, comprising: an electronic device; an ultraviolet absorbent enclosure for containing at least one part of the electronic device; at least one ultraviolet radiation source embedded within the ultraviolet absorbent enclosure, the at least one ultraviolet radiation source configured to generate ultraviolet radiation directed at the part of the electronic device; and a monitoring and control system for managing the ultraviolet radiation directed at the part of the electronic device by performing a method comprising: monitoring the electronic device for at least one of: a frequency of usage of the electronic device, a presence of biological activity on the electronic device and a disinfection schedule history for the electronic device; and controlling, based on the monitoring, the ultraviolet radiation directed at the part of the electronic device.

A third aspect of the invention provides an apparatus, comprising: an electronic device; an ultraviolet absorbent enclosure for containing at least one part of the electronic device; at least one ultraviolet radiation source embedded within the ultraviolet absorbent case, the at least one ultraviolet radiation source configured to generate ultraviolet radiation directed at the part of the electronic device; a switch on the ultraviolet absorbent enclosure to turn off the ultraviolet radiation when the part of the electronic device is not located within the ultraviolet absorbent enclosure; and a monitoring and control system for managing the ultraviolet radiation directed at the part of the electronic device by performing a method comprising: monitoring the electronic device for at least one of: a frequency of usage of the electronic device, a presence of biological activity on the electronic device and a disinfection schedule history for the electronic device; and controlling, based on the monitoring, the ultraviolet radiation directed at the part of the electronic device.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 10A-10B show an isometric view and a top view, respectively, of an ultraviolet radiation system for a laptop according to an embodiment.

FIG. 11 shows an isometric view of an ultraviolet radiation system for a laptop according to an embodiment.

FIGS. 12A-12C show an isometric view and cross-sectional views of an ultraviolet radiation system for a keyboard according to an embodiment.

FIG. 13 shows a cross-section of an illustrative light guiding structure that can be used in an ultraviolet radiation system for an electronic device according to an embodiment.

FIG. 14 shows a light guiding structure according to an alternative embodiment.

FIG. 15 shows an illustrative ultraviolet radiation system for an electronic device according to another embodiment.

FIGS. 16A-16C show an illustrative ultraviolet radiation system for an electronic device using at least one suction cup with ultraviolet light emitting diodes according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
FIG. 1 shows an illustrative electronic device within a case according to the prior art.

As indicated above, aspects of the invention provide a solution in which ultraviolet radiation is used to disinfect an electronic device. An ultraviolet radiation source is embedded within an ultraviolet absorbent case. While the electronic device is within the ultraviolet absorbent case, ultraviolent radiation is directed at the electronic device. A monitoring and control system monitors a plurality of attributes for the electronic device, which can include: a frequency of usage for the device, a biological activity at a surface of the device, and a disinfection schedule history for the device. Furthermore, the monitoring and control system can detect whether the device is being used. Based on the monitoring, the monitoring and control system controls the ultraviolet radiation directed at the electronic device.

As used herein, unless otherwise noted, the term "set" means one or more (i.e., at least one) and the phrase "any solution" means any now known or later developed solution. Furthermore, as used herein, ultraviolet radiation/light means electromagnetic radiation having a wavelength ranging from approximately 10 nanometers (nm) to approximately 400 nm, while ultraviolet-C (UV-C) means electromagnetic radiation having a wavelength ranging from approximately 100 nm to approximately 280 nm, ultraviolet-B (UV-B) means electromagnetic radiation having a wavelength ranging from approximately 280 to approximately 315 nanometers, and ultraviolet-A (UV-A) means electromagnetic radiation having a wavelength ranging from approximately 315 to approximately 400 nanometers. As also used herein, a material/structure is considered to be "reflective" to ultraviolet light of a particular wavelength when the material/structure has an ultraviolet reflection coefficient of at least thirty percent for the ultraviolet light of the particular wavelength. In a more particular embodiment, a highly ultraviolet reflective material/structure has an ultraviolet reflection coefficient of at least eighty percent. Furthermore, a material/structure is considered to be "transparent" to ultraviolet light of a particular wavelength when the material/structure allows a significant amount of the ultraviolet radiation to pass there through.

As used herein, the term "disinfection" and its related terms means treating the electronic device so that it includes a sufficiently low number of contaminants (e.g., chemical) and microorganisms (e.g., virus, bacteria, and/or the like) so that the electronic device can be handled as part of a desired human interaction with no or no reasonable risk for the transmission of a disease or other harm to the human. For example, disinfection of the electronic device means that the electronic device has a sufficiently low level of active microorganisms and/or concentration of other contaminants that a typical human can interact with the electronic device without suffering adverse effects from the microorganisms and/or contaminants present on the electronic device. In addition, disinfection can include sterilization. As used herein, the term "sterilization" and its related terms means neutralizing an ability of a microorganism to reproduce, which may be accomplished without physically destroying the microorganism. In this example, a level of microorganisms present on the electronic device cannot increase to a dangerous level and will eventually be reduced, since the replication ability has been neutralized. A target level of microorganisms and/or contaminants can be defined, for example, by a standards setting organization, such as a governmental organization.

Turning to the drawings, FIG. 1 shows an illustrative portable electronic device 1 partially within a case 2 according to the prior art. The electronic device 1 can include a mobile phone, a tablet, a music player, a laptop, a computer keyboard, and/or the like. In this example, the electronic device 1 is a mobile phone. The electronic device 1 can include any device capable of supporting a computer operating system, such as IOS, Windows, Unix, Linux, Android, and/or the like, and include an application that enables a user control interface. The case 2 is used to protect the electronic device 1 and can be easily carried by a user of the electronic device 1. To this extent, the case 2 provides a portable protective covering for the portable electronic device 1. In an embodiment, it is desirable for the case 2 to add only a small amount of weight and bulk to the electronic device 1 so as not to impede placement of the electronic device 1 in a larger carrying item, such as a pocket, a purse, a messenger bag, a tote bag, or the like. As mentioned above, unlike the case 2, current approaches at sterilizing electronic devices, including portable electronic devices such as the mobile phone 1, are relatively bulky stationary units that do not allow the user to carry the electronic device 1 while the electronic device 1 is being sterilized.

Figure 2:
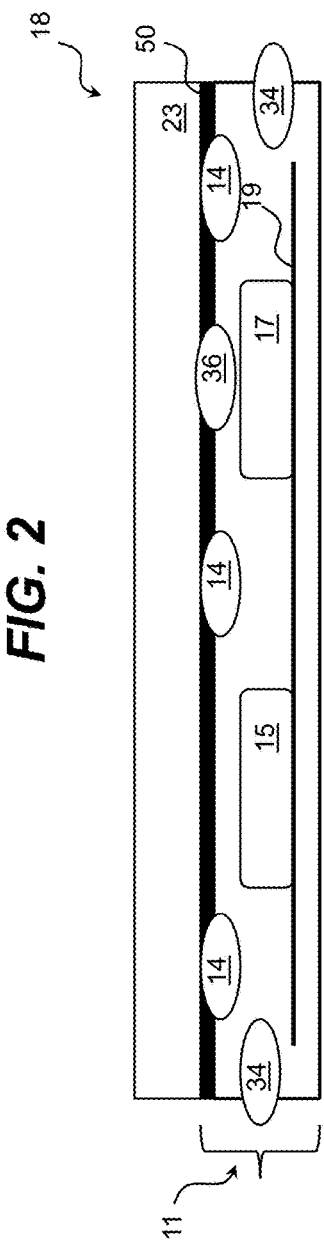
FIG. 2 shows a cross-sectional view of an illustrative ultraviolet absorbent case according to an embodiment.
Figure 3:
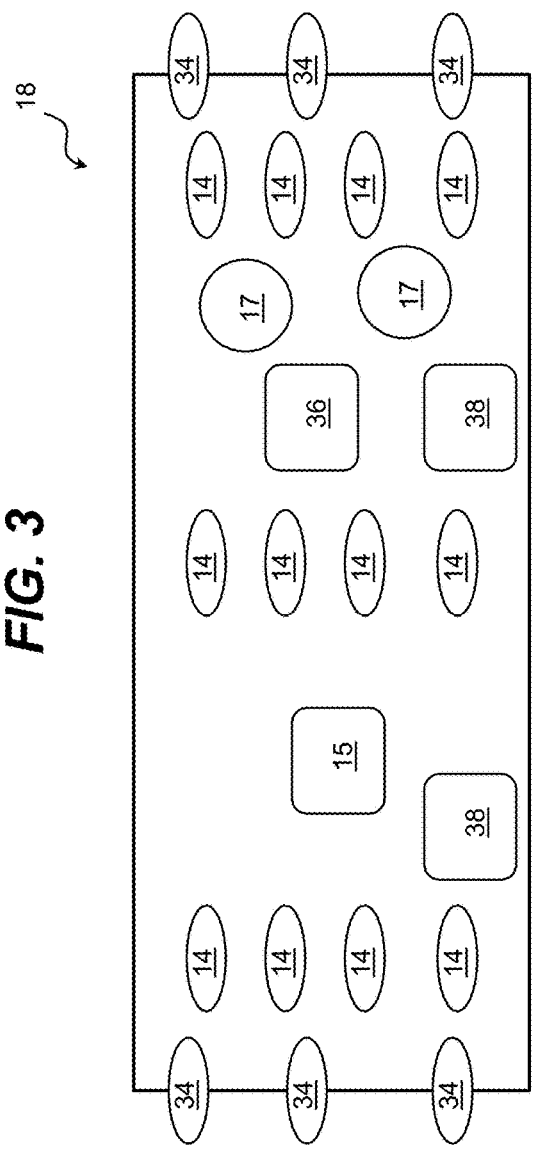
FIG. 3 shows a top view of an illustrative ultraviolet absorbent case according to an embodiment.

To this extent, FIGS. 2 and 3 show a cross-sectional view and a top view, respectively, of an illustrative ultraviolet absorbent case 18 for containing an electronic device, such as the electronic device 1 (FIG. 1), according to an embodiment. The ultraviolet absorbent case 18 is configured to provide for the disinfection of an electronic device 1 stored therein, while the user is carrying the electronic device 1 with him/her. To this extent, the ultraviolet absorbent case 18 can be configured to add a minimum amount of bulk/weight to the overall structure, so as to enable the user to continue to store the electronic device 1 in his/her preferred location (e.g., pocket, purse, etc.). The ultraviolet absorbent case 18 can be formed of any material capable of absorbing ultraviolet radiation to prevent a user from being harmed by the ultraviolet radiation. For example, the ultraviolet absorbent case 18 can be formed of polycarbonate, a transparent thermoplastic (e.g., Plexiglas), polyethylene, and/or the like. The ultraviolet absorbent case 18 includes a containment housing 23 that is used to physically contain the electronic device 1. In an embodiment, the containment housing 23 can be physically attached to the electronic device 1 using a solution similar to that of cases 2 (FIG. 1) of the prior art. An additional housing 11 can be permanently or temporarily attached to a front side of the containment housing 23 (e.g., the side opposite of where the electronic device 1 is inserted) using any solution. The additional housing 11 includes at least one ultraviolet radiation source 14 configured to generate ultraviolet radiation directed at the electronic device 1 contained by (e.g., located within, detachably attached adjacent to, and/or the like) the containment housing 23. In an embodiment, a plurality of layers 50 can be located between the containment housing 23 and the additional housing 11 to recycle the ultraviolet radiation generated by the ultraviolet radiation source 14 as described herein.

Figure 4A:
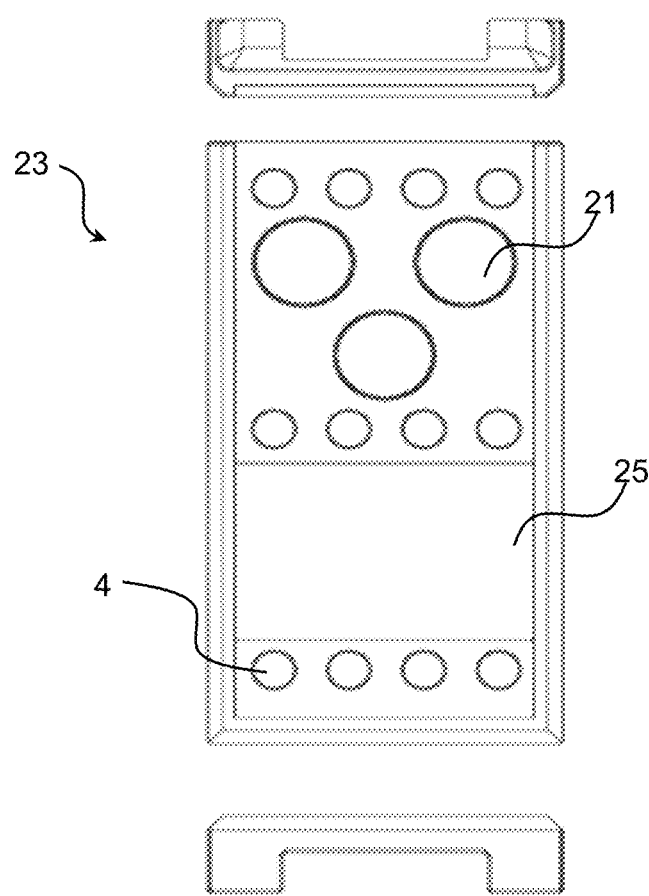
FIGS. 4A-4C show top, back side, and front side views of an illustrative containment housing of an illustrative ultraviolet absorbent case according to an embodiment.
Figure 4C:
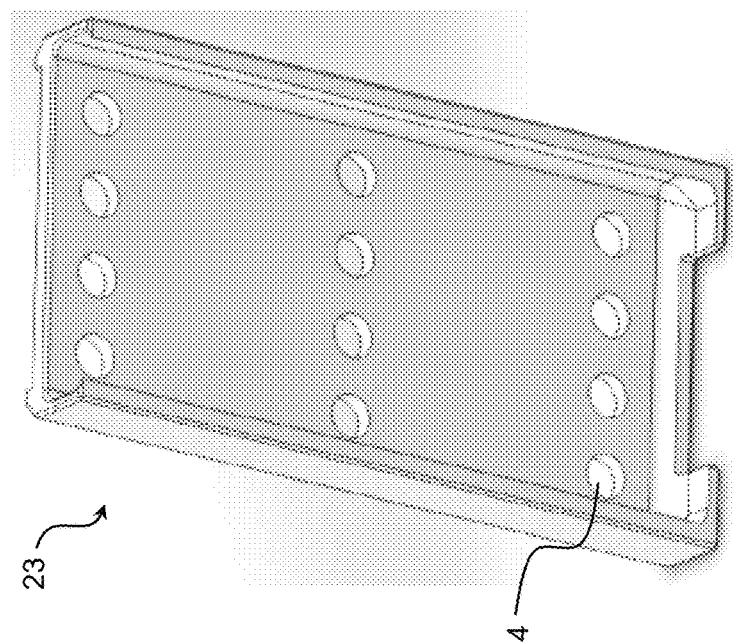
Figure 4B:
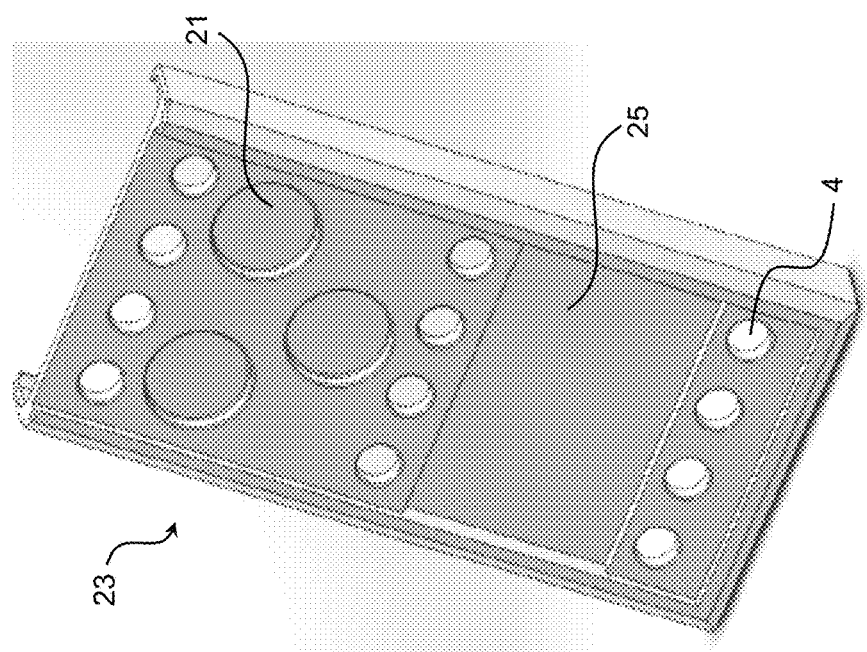

Turning now to FIGS. 4A-4C in conjunction with FIGS. 2 and 3, top (with corresponding end views), back side, and front side perspective views of the containment housing 23 according to an embodiment are shown. The containment housing 23 can include a plurality of indentations 21, 25 to provide space for a power component 17, and for the monitoring and/or controlling component 15, respectively. The containment housing 23 also includes at least one opening 4 (e.g., one opening 4 for each ultraviolet radiation source 14) that allows the ultraviolet radiation to penetrate inside of the containment housing 23 to the electronic device 1 located therein. The ultraviolet radiation source 14 can comprise any combination of one or more ultraviolet radiation emitters. For example, the ultraviolet radiation source 14 can include a high intensity ultraviolet lamp (e.g., a high intensity mercury lamp), an ultraviolet light emitting diode (LED), super luminescent LEDs, laser diodes, and/or the like. In an embodiment, the ultraviolet radiation source 14 includes a set of light emitting diodes manufactured with one or more layers of materials selected from the group-III nitride material system (e.g., $Al_xIn_yGa_{1-x-y}N$, where $0 \leq x, y \leq 1$, and $x+y \leq 1$ and/or alloys thereof). In an illustrative embodiment, the ultraviolet radiation source 14 can emit ultraviolet radiation in the range of approximately 200 nanometers to approximately 300 nanometers. Additionally, the ultraviolet radiation source 14 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like, at the electronic device 1. Illustrative wave guiding structures include, but are not limited to, a plurality of ultraviolet fibers, each of which terminates at an opening, a diffuser, and/or the like.

Returning now to FIGS. 2 and 3, the additional housing 11 further includes: at least one light emitting diode (LED) 34 for emitting visible light to indicate that ultraviolet radiation is being generated; a power component 17 (e.g., batteries); and a compartment for a monitoring and/or control component 15 (e.g., LED driver integrated circuits and/or power management integrated circuits) capable of delivering power from the power component 17 to the LED 34 and the at least one ultraviolet radiation source 14 and for controlling the LED 34 and at the least one ultraviolet radiation source 14. The additional housing 11 also can include a printed circuit board (PCB) 19 for mounting and connecting the power component 17 and the monitoring and/or control component 15. Still further, the additional housing 11 can include at least one sensor and/or switch 38 (FIG. 3) that provides data corresponding to a presence of the electronic device 1 within or attached to the containment housing 23 for use by the monitoring and/or control component 15. Although it is not shown in the figures, the exterior of the ultraviolet absorbent case 18 can include a plurality of fins, or the like, for enhanced heat extraction from the electronic components located in the additional housing 11. In an embodiment, deep UV (DUV) LEDs are assembled in multiple parallel strings, each of which contains multiple devices. A bias voltage range for operating the DUV LEDs in such a system can be in a range of four to thirty-two Volts. In an illustrative embodiment, a parallel arrangement of a single DUV LED with low dropout linear current drivers in series for each device allows for implementation of high redundancy schemes in disinfection systems.

Figure 5:
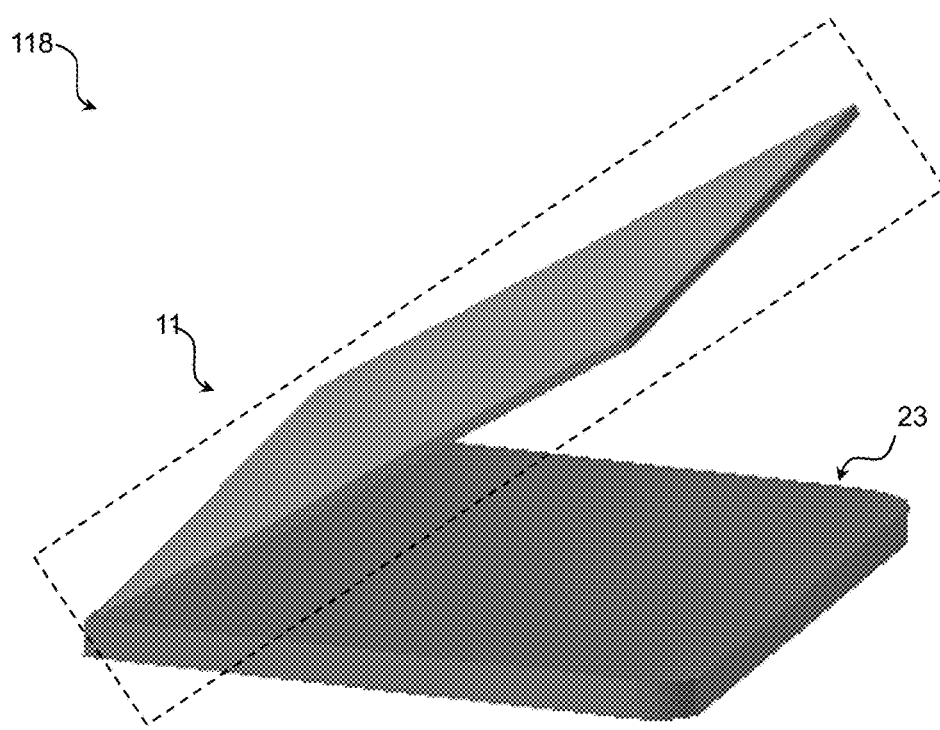
FIG. 5 shows an isometric view of an illustrative ultraviolet absorbent case according to an embodiment.

The additional housing 11 can be attached to the containment housing 23 using any of various attachment configurations. Turning now to FIG. 5, an isometric view of an ultraviolet absorbent case 118 according to an embodiment is shown. In this embodiment, the additional housing 11 is hingedly connected to the containment housing 23 along one side of the containment housing 23 using any type of hinged attachment mechanism. In one embodiment, the additional housing 11 can be magnetically attached/closed to the containment housing 23. Furthermore, when an electronic device 1 is located within or attached to the containment housing 23, and the additional housing 11 is closed against the front surface of the containment housing 23, a sensor and/or switch 38 located in the additional housing 11 can determine the presence of the electronic device 1, which the monitoring and/or control component 15 can use to turn on the ultraviolet radiation source 14 to disinfect the electronic device 1. However, when the sensor and/or switch 38 determines that the additional housing 11 is open, the monitoring and/or control component 15 can turn off the ultraviolet radiation source 14 to avoid harming any users.

Figure 6:
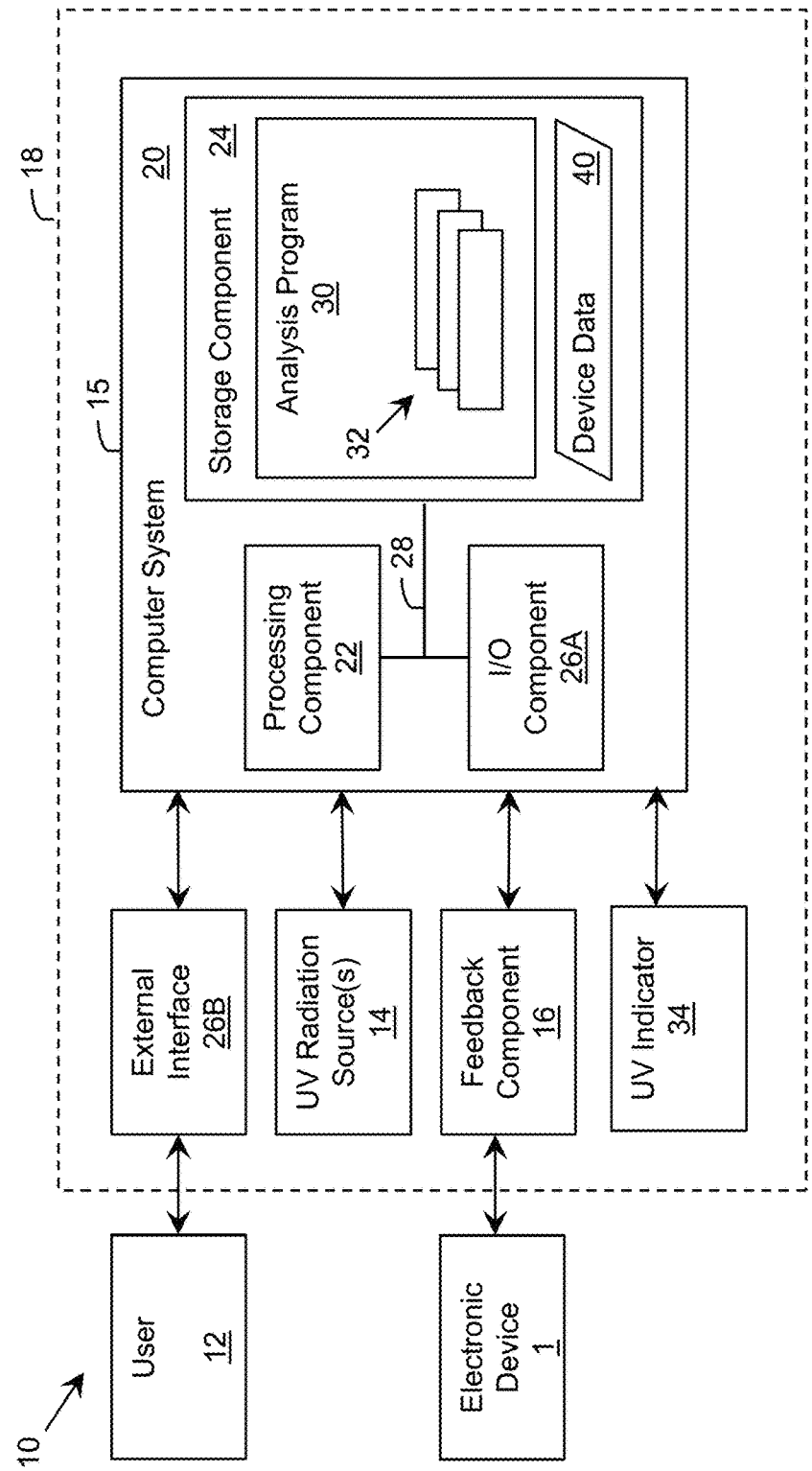
FIG. 6 shows an illustrative ultraviolet radiation system for an electronic device according to an embodiment.

Turning now to FIG. 6, an illustrative ultraviolet radiation system 10 according to an embodiment is shown. In this case, the system 10 includes a monitoring and/or control system 15 incorporated in the ultraviolet absorbent case 18, which is implemented as a computer system 20 including an analysis program 30, which makes the computer system 20 operable to manage an ultraviolet radiation source 14 by performing a process described herein. In particular, the analysis program 30 can enable the computer system 20 to operate the ultraviolet radiation source 14 to generate and direct ultraviolet radiation toward the electronic device 1 (FIG. 1) and process data corresponding to one or more attributes regarding the electronic device 1, which is acquired by a feedback component 16, and/or an ultraviolet radiation history stored as device data 40. While a single ultraviolet radiation source 14 is shown in this figure, it is understood that the ultraviolet absorbent case 18 can include any number of ultraviolet radiation sources 14, the operation of which the computer system 20 can separately manage using a process described herein. In the case of more than one ultraviolet radiation source 14, it is understood that the computer system 20 can individually control each ultraviolet radiation source 14 and/or control two or more of the ultraviolet radiation sources 14 as a group.

In an embodiment, during an initial period of operation (e.g., after an electronic device 1 is placed within or attached to the containment housing 23, and/or the like), the computer system 20 can acquire data from the feedback component 16 regarding one or more attributes of the electronic device 1 and generate device data 40 for further processing. The device data 40 can include a presence of biological activity (e.g., microorganisms, viruses, bacteria, and/or the like) on a surface of the electronic device 1, a usage history of the electronic device 1 (e.g., timestamps for the removal of and relocation of the electronic device 1 in the containment housing 23), a frequency of usage of the electronic device 1, a disinfection schedule history for the electronic device 1, and/or the like. The computer system 20 can use the device data 40 to control one or more aspects of the ultraviolet radiation generated by the ultraviolet radiation source(s) 14.

Furthermore, one or more aspects of the operation of the ultraviolet radiation source 14 can be controlled by a user 12 via an external interface component 26B. The external interface component 26B can be located on an exterior of the ultraviolet absorbent case 18 and allow the user 12 to choose when to turn on the ultraviolet radiation source 14. However, it is understood that the sensor and/or switch 38 (FIG. 3) must still determine the presence of the electronic device 1 and that the additional housing 11 is closed against the electronic device 1 to avoid harming the user 12. The external interface component 26B can include a touch screen that shows control dials for adjusting an intensity, scheduling, and other operational properties of the at least one ultraviolet radiation source 14. In an embodiment, the external interface component 26B can include a keyboard, a plurality of buttons, a joystick-like control mechanism, and/or the like, to control the at least one ultraviolet radiation source 14.

The computer system 20 is shown including a processing component 22 (e.g., one or more processors), a storage component 24 (e.g., a storage hierarchy), an input/output (I/O) component 26A (e.g., one or more I/O interfaces and/or devices), and a communications pathway 28. In general, the processing component 22 executes program code, such as the analysis program 30, which is at least partially fixed in the storage component 24. While executing program code, the processing component 22 can process data, which can result in reading and/or writing transformed data from/to the storage component 24 and/or the I/O component 26A for further processing. The pathway 28 provides a communications link between each of the components in the computer system 20. The I/O component 26A and/or the external interface component 26B can comprise one or more human I/O devices, which enable a human user 12 to interact with the computer system 20 and/or one or more communications devices to enable a system user 12 to communicate with the computer system 20 using any type of communications link. To this extent, during execution by the computer system 20, the analysis program 30 can manage a set of interfaces (e.g., graphical user interface(s), application program interface, and/or the like) that enable human and/or system users 12 to interact with the analysis program 30. Furthermore, the analysis program 30 can manage (e.g., store, retrieve, create, manipulate, organize, present, etc.) the data, such as device data 40, using any solution.

In any event, the computer system 20 can comprise one or more general purpose computing articles of manufacture (e.g., computing devices) capable of executing program code, such as the analysis program 30, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 30 can be embodied as any combination of system software and/or application software.

Furthermore, the analysis program 30 can be implemented using a set of modules 32. In this case, a module 32 can enable the computer system 20 to perform a set of tasks used by the analysis program 30, and can be separately developed and/or implemented apart from other portions of the analysis program 30. When the computer system 20 comprises multiple computing devices, each computing device can have only a portion of the analysis program 30 fixed thereon (e.g., one or more modules 32). However, it is understood that the computer system 20 and the analysis program 30 are only representative of various possible equivalent monitoring and/or control systems 11 that may perform a process described herein. To this extent, in other embodiments, the functionality provided by the computer system 20 and the analysis program 30 can be at least partially implemented by one or more computing devices that include any combination of general and/or specific purpose hardware with or without program code. In each embodiment, the hardware and program code, if included, can be created using standard engineering and programming techniques, respectively. In another embodiment, the monitoring and/or control system 15 can be implemented without any computing device, e.g., using a closed loop circuit implementing a feedback control loop in which the outputs of one or more sensing devices are used as inputs to control the operation of one or more other devices (e.g., LEDs). Illustrative aspects of the invention are further described in conjunction with the computer system 20. However, it is understood that the functionality described in conjunction therewith can be implemented by any type of monitoring and/or control system 15.

Regardless, when the computer system 20 includes multiple computing devices, the computing devices can communicate over any type of communications link. Furthermore, while performing a process described herein, the computer system 20 can communicate with one or more other computer systems, such as the user 12, using any type of communications link. In either case, the communications link can comprise any combination of various types of wired and/or wireless links; comprise any combination of one or more types of networks; and/or utilize any combination of various types of transmission techniques and protocols.

The system 10 also can include an ultraviolet radiation indicator 34 (e.g., an LED), which can be operated by the computer system 20 to indicate when ultraviolet radiation is being generated and directed at the electronic device 1 within the ultraviolet absorbent case 18. The ultraviolet radiation indicator 34 can include one or more LEDs for emitting a visual light for the user 12.

Figure 7:
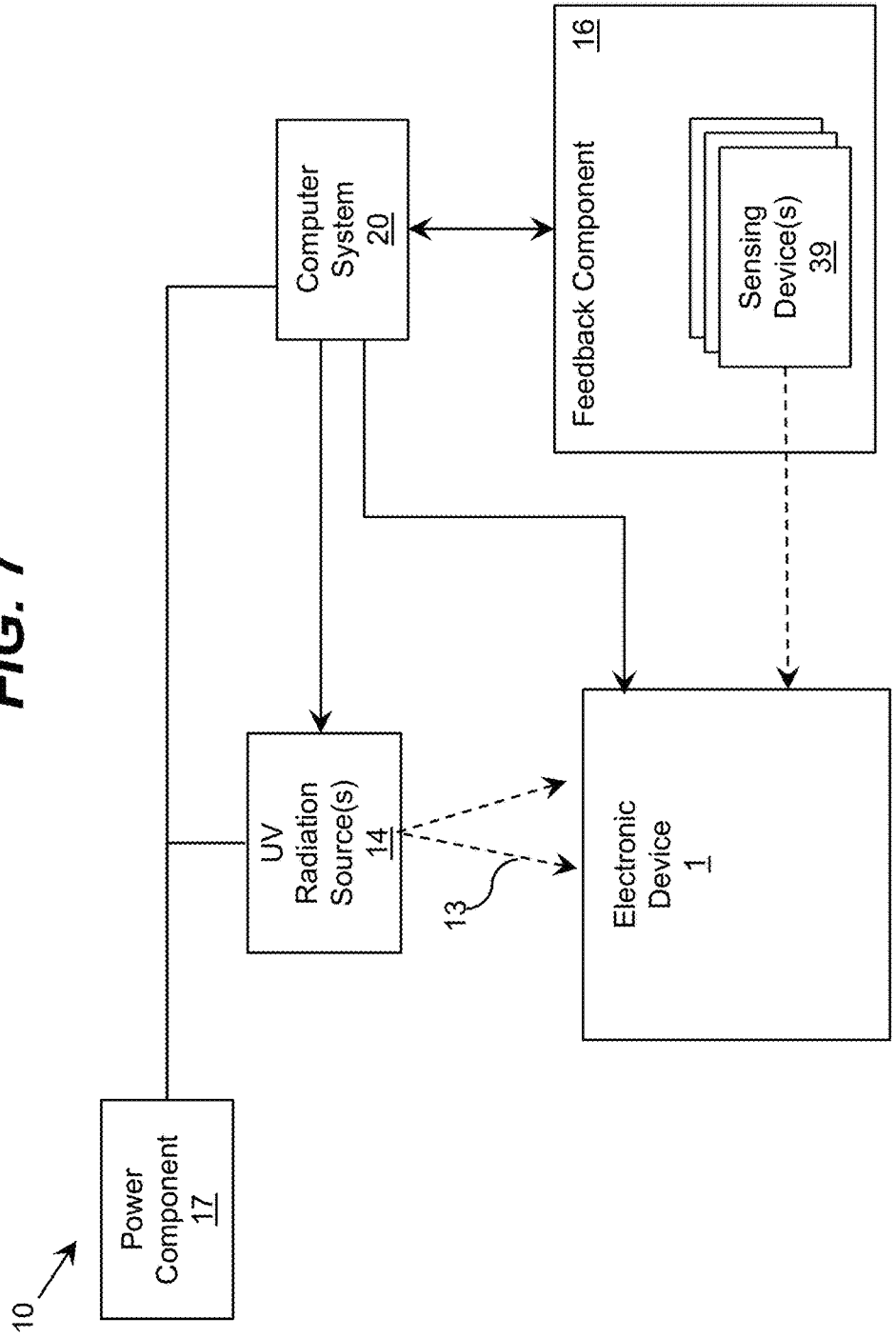
FIG. 7 shows an illustrative system including an ultraviolet radiation system for an electronic device according to an embodiment.

Turning now to FIG. 7, an illustrative system including an ultraviolet radiation system 10 for the electronic device 1 is shown. The computer system 20 is configured to control the ultraviolet radiation source 14 to direct ultraviolet radiation 13 at the electronic device 1. The feedback component 16 is configured to acquire data used to monitor a plurality of attributes regarding the electronic device 1 over a period of time. As illustrated, the feedback component 16 can include a plurality of sensing devices 39, each of which can acquire data used by the computer system 20 to monitor the set of attributes.

It is understood that the plurality of attributes for the electronic device 1 can include: a frequency of the usage of the electronic device 1, a presence of biological activity on the electronic device 1, a usage of the electronic device, a disinfection schedule history for the electronic device 1, and/or the like. In the case of determining usage details for the electronic device 1, a sensing device 39 can include a sensor and/or a switch 38 (FIG. 3) to sense that an electronic device 1 is physically contained within the containment housing 23. Alternatively, the sensor and/or switch 38 can sense that the electronic device 1 is not located within the containment housing 23 and assume that the electronic device 1 is being used.

In the case of determining a presence of biological activity on the electronic device 1, the sensing devices 39 can also determine a location of the biological activity, a type of biological activity (e.g., type of organism), a concentration of the biological activity, an estimated amount of time an organism has been in a growth phase (e.g., exponential growth and/or stationary), and/or the like. Furthermore, the sensing device 39 can determine information on the variation of the biological activity over time, such as a growth rate, a rate with which an area including the biological activity is spreading, and/or the like. In an embodiment, a set of biological activity dynamics are related to various attributes of bacteria and/or virus activity on the electronic device 1, including, for example, the presence of detectable bacteria and/or virus activity, measured bacteria and/or virus population/concentration time dynamics, growth phase, and/or the like.

In an embodiment, to determine the presence of biological activity on the electronic device 1, the sensing devices 39 include at least one of a visual camera or a chemical sensor 36 (FIG. 3). The visual camera can acquire visual data (e.g., visual, electronic, and/or the like) used to monitor the electronic device 1, while the chemical sensor can acquire chemical data (e.g., chemical, electronic, and/or the like) used to monitor the electronic device 1. For example, when the computer system 20 is operating the ultraviolet radiation source 14, a visual camera and/or a chemical sensor 36 monitoring the electronic device 1 may be operated to detect the presence of microorganisms. In a specific embodiment, the visual camera 36 comprises a fluorescent optical camera that can detect bacteria and/or viruses that become fluorescent under ultraviolet radiation. However, it is understood that a visual camera and a chemical sensor are only illustrative of various types of sensors that can be implemented. For example, the sensing devices 39 can include one or more mechanical sensors (including piezoelectric sensors, various membranes, cantilevers, a micro-electromechanical sensor or MEMS, a nanomechanical sensor, and/or the like), which can be configured to acquire any of various types of data regarding the electronic device 1.

The computer system 20 can be configured to control and adjust a direction, an intensity, a pattern, and/or a spectral power (e.g., wavelength) of the at least one ultraviolet radiation source 14, based on the feedback component 16. The computer system 20 can control and adjust each property of the ultraviolet radiation source 14 independently. For example, the computer system 20 can adjust the intensity, time duration, and/or time scheduling (e.g., including duration (e.g., exposure/illumination time)), duty cycle, time between exposures/illuminations, and/or the like) of the ultraviolet radiation source 14 for a given wavelength. Each of the properties of the ultraviolet radiation source 14 can be adjustable and controlled by the computer system 20 according to data provided by the feedback component 16.

For example, the computer system 20 can be configured to adjust the direction of the ultraviolet radiation according to a location of the biological activity detected on the electronic device 1 by the sensing device(s) 39 using any solution. The computer system 20 can be configured to utilize a target timing, intensity, and/or spectral power of the ultraviolet radiation according to a type of biological activity. That is, the sensing devices 39 can sense locations of higher levels of biological activity on the electronic device 1, and the ultraviolet radiation source 14 can be configured by the computer system 20 to direct higher doses (by increasing intensity or exposure) of ultraviolet radiation at the locations with higher levels of biological activity (e.g., non-uniform ultraviolet radiation).

The sensing devices 39 can also sense (via sensor and/or switch 38) that the electronic device 1 is physically contained within the containment housing 23. In response to detection of the electronic device 1 being located within the containment housing 23, the computer system 20 can be configured to automatically turn on the ultraviolet radiation. In one embodiment, the computer system 20 can be configured to set a periodic or an aperiodic schedule for the ultraviolet radiation when the electronic device 1 is within the containment housing 23. This (periodic or aperiodic) schedule can be interrupted when the sensing device 39 senses that the electronic device 1 is removed from the containment housing 23 and the computer system 20 can be configured to turn off the ultraviolet radiation. In this case, the schedule (periodic or aperiodic) can be resumed once the sensing device 39 senses the electronic device 1 within the containment housing 23 again.

It is understood that the system 10 may include a power component 17 that is implemented separately from the electronic device 1 to supply power to one or more of the various components of system 10, such as ultraviolet radiation sources 14, feedback component 16, computer system 20, and/or the like. For example, the electronic device 1 may comprise a power source that is insufficient to operate the various devices of system 10 in addition to maintaining sufficient power to continue one or more aspects of the operation of the electronic device 1. Regardless, the power component 17 can be utilized to operate system 10. The power component 17 can be embedded in the additional housing 11 (FIG. 2) along with the at least one ultraviolet radiation source 14. The power component 17 can comprise any source of power including, but not limited to, a battery set, a solar cell, and/or the like. For example, the power component 17 can include any of various types of rechargeable batteries (e.g., lithium ion, nickel-cadmium, and/or the like). The power component 17 can be configured for operation of high efficiency direct current (DC) step-up/boost converters. In an embodiment, the power component (e.g., conversion efficiency and maximum battery life) is configured (e.g., optimized) to keep a difference between the electrical power available versus the electrical power required for the various components at the minimum. In an embodiment, the power component comprises a battery set that is capable of being recharged through a typical household outlet. A charging system for this embodiment can comprise an electrical cord for charging that can include, for example, a cord with a Universal Serial Bus (USB) connection.

In an embodiment, the computer system 20 can implement multiple modes of operation depending on the source of power and/or an amount of power remaining. In particular, when a power component 17 of limited capacity is being utilized, one or more functions of system 10 can be disabled and/or reduced to lengthen an operating time for system 10. In another embodiment, a data-electrical link can be made between the electronic device 1 and the ultraviolet absorbent case 18 (FIG. 6) for data and/or power exchange between the electronic device 1 and the computer system 20. For example, the electronic device 1 and the ultraviolet absorbent case 18 can be charged simultaneously via this data-electrical link. Additionally, the computer system 20 can provide data (via wireless and/or wired means) regarding the disinfection of the electronic device 1 to the electronic device 1, which can be presented to the user 12 (e.g., via an app installed on the electronic device 1). In another embodiment, the power component 17 can comprise an electrical cord for charging the ultraviolet absorbent case 18 via a household outlet.

Figure 8:
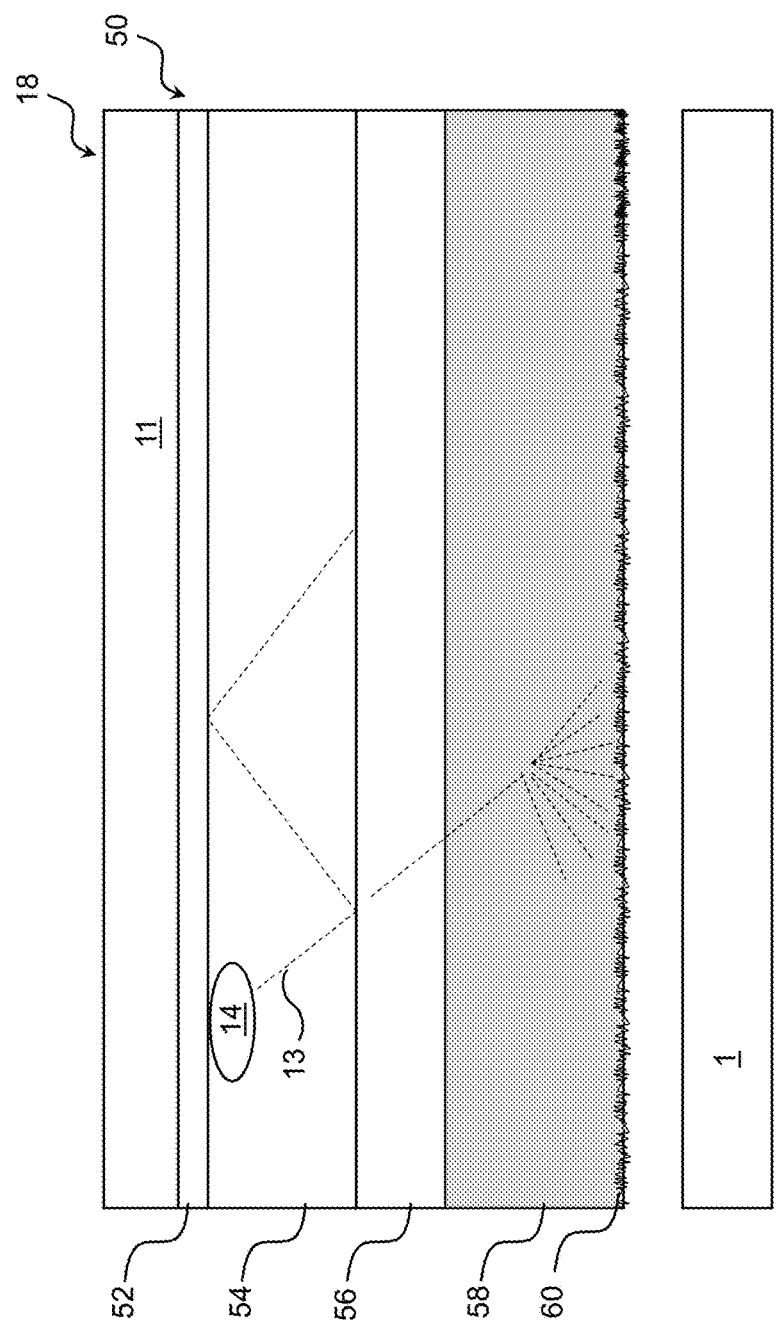
FIG. 8 shows a cross-sectional view of an illustrative configuration of a plurality of reflective layers for recycling ultraviolet radiation of an ultraviolet radiation system according to an embodiment.

Turning now to FIG. 8, a cross-sectional view of an illustrative configuration of the plurality of layers 50 (FIG. 2) located between the additional housing 11 and the containment housing 23 (FIG. 2) is shown. It is assumed that the electronic device 1 is contained within the containment housing 23. Other features of the additional housing 11 are omitted in this figure for clarity. The plurality of layers 50 are configured to recycle the ultraviolet radiation 13 generated by each ultraviolet radiation source 14 and uniformly distribute the radiation across the electronic device 1. The plurality of layers 50 can include a wave-guiding reflective layer 52 to further transmit the ultraviolet radiation 13. In an embodiment, the wave-guiding reflective layer 52 can include a reflective material such as aluminum (highly polished). In an alternative embodiment, the wave-guiding reflective layer 52 can include a low refractive index material for total internal reflection. A first partially transmitting, partially reflective layer 54 and a second partially transmitting, partially reflective layer 58 are located below the wave-guiding reflective layer 52. These layers 54, 58 can include materials such as fused silica, sapphire, and any other ultraviolet transparent material.

A partial reflectivity of layers 54, 58 can be between 5 to 100% and at least some of the ultraviolet radiation can experience reflectivity higher than 80% (e.g., at least 5% of all the ultraviolet radiation). The partial transmitting feature of layers 54, 58 can be for at least 50% of the ultraviolet radiation. The interface between the first partially transmitting, partially reflective layer 54 and the second partially transmitting, partially reflective layer 58 can split a beam of the ultraviolet radiation 13 by allowing a portion to pass to layer 58 and reflecting a portion back into layer 54. This can be due to a frustrated total internal reflection of the ultraviolet radiation 13. For frustrated total internal reflection, the ultraviolet radiation source 14 is oriented at an angle to the interface that is greater than 10 degrees. The interface of layer 54 and layer 58 can include a layer 56, which comprises a thin layer of material including a low index of refraction, so that the ultraviolet radiation 13 is partially transmitted through to layer 58 and partially reflected back into layer 54. In another embodiment, a partially (e.g., half) silvered interface can be located between layer 54 and layer 58 to partially transmit and partially reflect the ultraviolet radiation 13. The layer 58 includes a diffusing interface 60 to facilitate scattering of the ultraviolet radiation 13 as it exits the plurality of layers 50.

Figure 9:
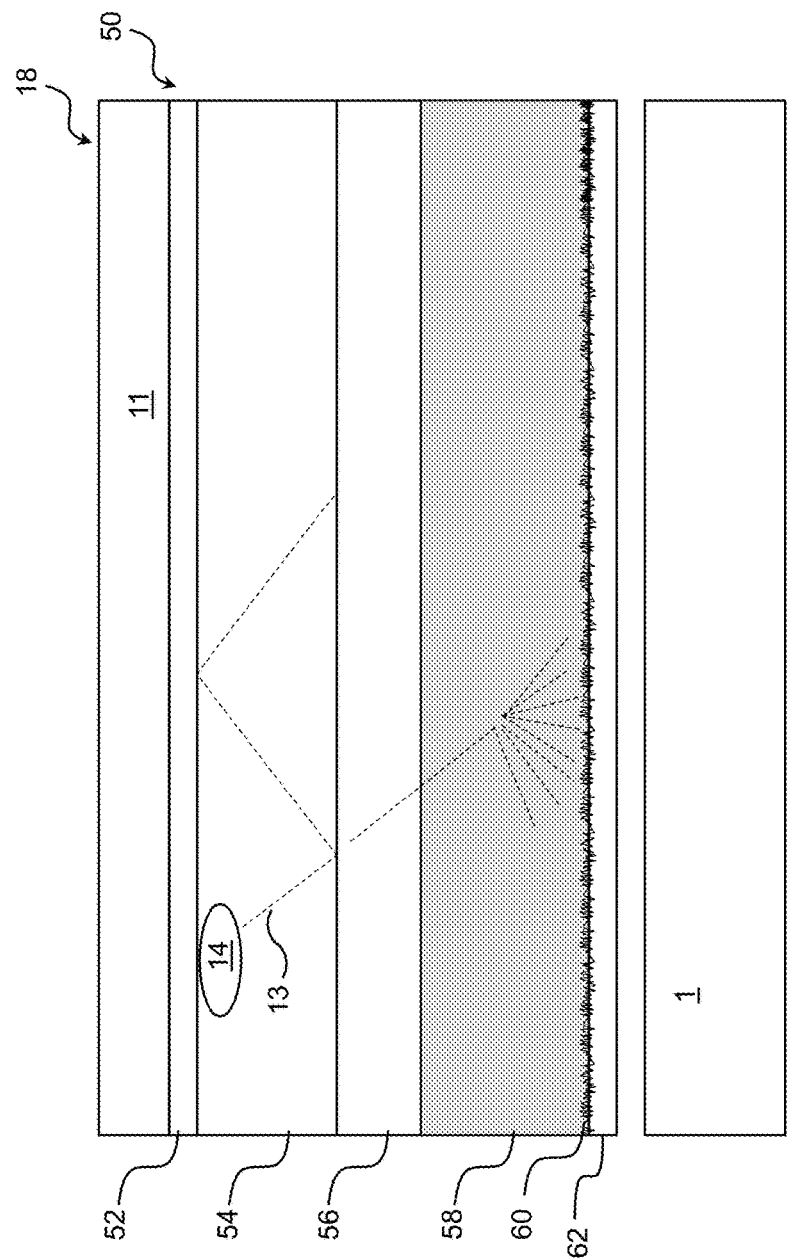
FIG. 9 shows a cross-sectional view of a plurality of reflective layers for recycling ultraviolet radiation of an ultraviolet radiation system according to an embodiment.

Turning now to FIG. 9, an antibacterial layer 62 can be located below the diffusing interface 60. The antibacterial layer 62 can be activated by visible or infrared radiation. The antibacterial layer 62 can include materials that are activated by particular wavelengths, such as indocyanine green (808 nm), and/or the like. The antibacterial layer 62 can also include a $TiO_2$-anatase photocatalyst, which can be activated by either visible light or ultraviolet radiation. In this case, the antibacterial layer 62 comprises a wide band-gap (e.g., 3.0-3.2 eV) semiconductor that generates energy-rich electron-hole pairs, which results in the formation of hydroxide and other oxidizing radicals, which are able to degrade cell components of microorganisms under ultraviolet radiation. In one embodiment, the antibacterial layer 62 can contact the electronic device 1 to enhance an overall efficiency of the disinfection system. However, it is not required that the antibacterial layer 62 contact the electronic device 1.

Turning now to FIGS. 10A-10B, an isometric view and a top view, respectively, of an ultraviolet radiation system for a laptop 100 according to an embodiment is shown. The ultraviolet absorbent case 218 for the laptop 100 includes a pocket 70 for inserting the lid portion of the laptop 100 including the screen. Turning to FIG. 11, the pocket includes one or more locations into which ultraviolet radiation source(s) 14 are embedded. The pocket 70 can include an opening for the screen of the laptop 100, so that the screen is not obscured when the lid of the laptop 100 is inserted into the pocket 70. A middle pad 76 can be provided for separately disinfecting the laptop keyboard. The middle pad 76 can be sufficiently thin enough to allow the lid of the laptop 100 to be closed while the middle pad 76 is present. The middle pad 76 can comprise, for example, a surface comprising leaky optical fibers that are capable of delivering ultraviolet radiation to the lid and/or keyboard surfaces of the laptop 100. In this embodiment, the ultraviolet radiation sources, and control mechanisms can be outside the middle pad 76 area and connected to the middle pad 76 via optical fibers.

Returning to FIGS. 10A and 10B, the ultraviolet absorbent case 218 can also include a plurality of flexible ultraviolet absorbing side flaps 72A, 72B, 72C and a bottom pocket 74 for the laptop assembly and keyboard. The side flaps 72A, 72B, 72C can connect to the backside of the pocket 70 by any attachment means, such as Velcro and/or the like to prevent ultraviolet radiation from escaping. A switch (not shown) can be activated when the side flaps 72A, 72B, 72C are opened to turn off the ultraviolet radiation and/or prevent the ultraviolet radiation from being turned on.

Turning now to FIGS. 12A-12C, various views of an ultraviolet absorbent case 318 for disinfecting a keyboard 200 are shown. The case 318 can include a profile that matches (e.g., is the inverse of) the profile of the keyboard, as seen in FIG. 12B. An ultraviolet radiation source, such as a LED 14A, can be used to disinfect keyboard keys, while optical fibers 14B can be used to disinfect the vacancies between keyboard keys. In another embodiment, a brush of optical fibers 14C can be used to disinfect the keyboard 200.

For each embodiment of the ultraviolet absorbent case, the case can be configured to provide at least a target amount of mechanical protection for the electronic device 1. For example, the target amount of mechanical protection can provide at least one meter drop protection for the electronic device 1, which can be measured by a drop test. The drop test can include dropping the electronic device within the ultraviolet absorbent case from a height of approximately one meter. This drop test can be performed multiple times, while capturing images of the landing each time. The electronic device 1 and ultraviolet system can be tested after each drop to ensure the performance capabilities remain unchanged. In an embodiment, the case can include a material that absorbs the impact from the drop. For instance, the case can be made of rubber or plastic. Additionally, the material can be rubberized polycarbonate, polycarbonate, an acrylonitrile butadiene styrene (ABS) composite, polyurethane composites, and/or the like.

For each embodiment of the ultraviolet absorbent case, the case can be configured to provide at least a target amount of waterproof protection for the electronic device 1. For example, the waterproof protection can provide at least a timed submersion protection for the electronic device 1, which can be measured by a water test. The water test can include submerging the electronic device 1 located within the ultraviolet absorbent case into water for a duration of 10 seconds after which the performance capabilities of the electronic device 1 and ultraviolet system can be evaluated. This water test can be performed multiple times between each evaluation, or performed once before each evaluation. The waterproof protection can be implemented using any solution. For example, the case can include a water tight seal between the electronic device 1 and the ultraviolet absorbent case 18. The seal can provide both ultraviolet radiation protection for the user and water protection for the electronic device 1. In an embodiment, the seal can include a gasket that seals a space between the electronic device 1 and the case 18 to prevent moisture and/or water from reaching the electronic device 1. For example, the water protective material can comprise rubber, fluorinated ethylene propylene (FEP), polytetrafluoroethylene (PTFE, such as Teflon), ultraviolet resistant polycarbonate, an ultraviolet resistant transparent thermoplastic, and/or the like.

While shown and described herein as a method and system for disinfecting an electronic device, it is understood that aspects of the invention further provide various alternative embodiments. For example, in one embodiment, the invention provides a computer program fixed in at least one computer-readable medium, which when executed, enables a computer system to disinfect the electronic device using a process described herein. To this extent, the computer-readable medium includes program code, such as the analysis program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

FIG. 13 shows a cross-section of an illustrative light guiding structure 78 that can be used in an ultraviolet radiation system for an electronic device 1 according to an embodiment. In particular, FIG. 13 shows that the light guiding structure 78 can take the form of a multi-layer structure with multiple layers 80A-80G used to deliver ultraviolet radiation to the surface of various parts (e.g., 3A and 3B) of the electronic device 1. Layers 80A, 80C, 80E, and 80G can be formed of any suitable type of transparent material. For example, when the radiation is ultraviolet radiation, the material can be an ultraviolet transparent fluoropolymer-based film material. As used herein, a material that is ultraviolet transparent means the material transmits at least thirty percent of the radiation emitted normal to a surface of the material. Illustrative fluoropolymers capable of being utilized to form the light guiding structure 78 include: fluorinated ethylene-propylene (EFEP), fluorinated ethylene propylene (FEP), perfluoroalkoxy (PFA), tetrafluoroethylene hexafluoropropylene vinylidene fluoride (THV), polytetrafluoroethylene (PTFE), polyvinylidene fluoride (PVDF), ethylene-tetrafluoroethylene (ETFE), ethylene chlorotrifluoroethylene (ECTFE), polychlorotrifluoroethene (PCTFE), a copolymer of tetrafluoroethylene and perfluoromethylvinylether (MFA), low density polyethylene (LDPE), perfluoroether (PFA), an amorphous fluoroplastic resin (e.g., Teflon AF 2400), and/or the like. While primarily described in conjunction with fluoropolymers, it is understood that other comparable materials can be utilized. Illustrative materials include polylactide (PLA), fused silica, sapphire, THE, and/or the like.

Each layer 80A, 80C, 80E, and 80G can have a thickness, which is sufficiently thin to provide a desired level of transparency. For example, a layer 80A, 80C, 80E, and 80G can be formed of TEFLON AF 2400 and have a thickness of several micrometers (e.g., ten micrometers or less) or even several tens of micrometers (e.g., forty micrometers or less). In one embodiment, the thickness and optical absorption of a fluoropolymer film used for layers 80A, 80C, 80E, and 80G can be selected to allow at least 20% transmission to the ultraviolet radiation normal to the film surface. An illustrative solution for fabricating such fluoropolymer layers is shown, for example, in U.S. Pat. No. 7,914,852, which is hereby incorporated by reference. Another solution for fabricating a light guiding structure described herein is shown and described in U.S. Provisional Application No. 62/050,126. In an embodiment, the fluoropolymer is applied onto a thin layer of fused silica. In an embodiment, selection of the thicknesses and/or refractive indexes of the materials is performed using a genetic algorithm. In this case, multiple possible combinations of values are evaluated with a subset of the best performing values used, along with some randomness, to create a new group of values to be evaluated. Such a process can be repeated any number of times to arrive at a set of values.

Regardless, the light guiding structure 78 includes layers 80B, 80D, and 80F, which are filled with a transparent fluid. In an embodiment, layers 80B and 80F are filled with a transparent gas while the layer 80D is filled with a transparent liquid. In an embodiment, the gas in the layers 80B and 80F can have a low refractive index (e.g., at most ninety percent of the refractive index of the material forming the adjacent layers 80A, 80C, 80E, and 80G), such as ambient air.

In an embodiment, the liquid in the layer 80D is substantially transparent to ultraviolet radiation and serves as light guiding layer in the structure 78. In this manner, the light guiding structure 78 can utilize total internal reflection to propagate the light there through. In this case, the fluid in the layer 80D has a transparency at least similar (e.g., within ten percent) to the transparency of purified water for light wavelengths in the range of 240 nanometers to 360 nanometers. In an embodiment, the fluid in the layer 80D is purified water as defined by the U.S. Food and Drug Administration.

For a layer 80B and 80F including a gas, the light guiding structure 78 can further include a corresponding set of pillars 82A, 82B. The pillars 82B, 82F also can be formed of a fluoropolymer-based material described herein. The pillars 82B, 82F can be configured to maintain a shape of the corresponding low refractive index guiding layer 80B, 80F, respectively. To this extent, the pillars 82A, 82B can be located in any pattern/random arrangement and can have any combination of one or more sizes and/or shapes, which is suitable for providing a desired amount of support. While not shown, it is understood that any fluid-filled layer, such as the layer 80D, can include a set of pillars. In an embodiment, the pillars 82A, 82B comprise diffusive elements. In this case, as illustrated, the diffusive elements start at one layer, such as the layer 80A, extend through a layer 80B, and end at another layer 80C. When both sets of pillars 82A, 82B are included, the pillars 82A can be staggered in relation to the pillars 82B.

As illustrated in FIG. 13, an ultraviolet radiation source 14 (e.g., an ultraviolet radiation emitter) can be coupled to the light guiding structure 78 at a location adjacent to a side 86 of the light guiding structure 78. A coupling mechanism 88 can be used to attach the ultraviolet radiation source 14 to the light guiding structure 78. In this manner, the coupling mechanism 88 can be configured to hold the ultraviolet radiation source 14 in a position such that light enters the light guiding structure 78 at an angle optimal for wave guiding, e.g., at an angle larger than the total internal reflection angle for the light guiding structure 78. In an embodiment, at least thirty percent of the light generated by the ultraviolet radiation source 14 is guided along the layer 80D. In an embodiment, the coupling mechanism 88 is a domain formed of a fluoropolymer-based material described herein, in which the ultraviolet radiation source 14 is embedded. While only a single ultraviolet radiation source 14 is shown, it is understood that any number of ultraviolet radiation source 14 can be coupled to the light guiding structure 78 in any of various possible combinations of locations.

One or more layers 80A-80G of the light guiding structure 78 can include a set of protrusions or diffusive elements 84A, 84B associated therewith, which are configured to allow light to propagate through an emission surface 90 out of the light guiding structure 78 in a diffusive manner towards the surfaces of parts 3A and 3B of the electronic device 1. For example, the layer 80A is shown including a set of diffusive elements 84A, and the layer 80C is shown including a set of diffusive elements 84B. As illustrated, the diffusive elements 84A can be located on an outer surface of the layer 80A forming the emission surface 90. Embodiments of diffusive elements 84A, 84B described herein can have any of various shapes including: truncated cone, lens, sphere, pyramid, inverted truncated cone, inverted pyramid, and/or the like. Furthermore, it is understood that a set of diffusive elements 84A, 84B can include a combination of diffusive elements of two or more different shapes. The diffusive elements 18A, 18C can be formed using any solution, such as surface patterning or roughening, welding/fusing the diffusive elements 84A, 84C to the corresponding layer 22A, 22C, and/or the like.

In an embodiment, each diffusive element 84A, 84B is capable of diffusive transmission/reflection of the radiation approximating a Lambertian distribution. In particular, an angular distribution of intensity of radiation transmitted/reflected from the diffusive element 84A, 84C can be normalized by total emitted power and compared to the Lambertian distribution. As used herein, the distribution approximates a Lambertian distribution when the deviation from the Lambertian distribution at each emitted angle is less than forty percent. The distribution substantially approximates a Lambertian distribution when the deviation is less than ten percent from a Lambertian distribution at each emitted angle. Furthermore, a distance between two adjacent diffusive elements 84A, 84B located on a surface can be selected to be smaller than an effective area of a surface illuminated by the diffusive radiation transmitted/reflected by the diffusive element 84A, 84B. To this extent, the spacing can be determined based on the distribution of the radiation from a diffusive element 84A, 84B as well as a target distance between the diffusive element 84A, 84B and a surface of an object being illuminated. Furthermore, when implemented as part of a disinfection system as described, spacing between adjacent diffusive elements 84A, 84B can be determined based on an expected spatial density of contamination on a surface to be disinfected. In this case, the distance can be inversely proportional to the expected spatial density of contamination.

Additionally, one or more of the layers 80A, 80C, 80E, and 80G can be formed of and/or coated with a reflective material. When utilized, a reflective coating can be located over an entirety of the layer 80A, 80C, 80E, and 80G or only a portion of the layer 80A, 80C, 80E, and 80G. Furthermore, the reflective coating can be located on either the outermost or innermost surface of the layer 80A, 80C, 80E, and 80G.

U.S. Provisional Patent Application 62/050,331, filed on 15 Sep. 2014, titled "UV Diffusive Lighting with a Waveguide provide more details of a light guiding structure and is hereby incorporated by reference.

It is understood that the surfaces of parts 3A and 3B of the electronic device 1 that receive the light from the light guiding structure 78 may have been determined beforehand, by for example, the ultraviolet radiation system, to be in need of disinfection, sterilization and/or like. However, light emitted from the ultraviolet radiation source 14 can be directed to other parts of the electronic device by the light guiding structure 78. Furthermore, it is understood that the ultraviolet radiation source 14 and the light guiding structure 78 can direct light in any pattern and direction to facilitate disinfection of any part of the electronic device 1 that is need of such an operation.

FIG. 14 shows a light guiding structure 92 according to an embodiment in use with an ultraviolet radiation system. In one embodiment, the light guiding structure 92 can include a light guiding layer 94 and a set of ultraviolet radiation sources 14 configured in a predetermined angular orientation with respect to the electronic device 1 in order to emit light 96 at a predetermined angular distribution to an underlying surface 98 of the device 1 that is in need of a treatment such as disinfection, sterilization, sanitization, and the like. In one embodiment, the light guiding layer 94 can include any one of the aforementioned partially ultraviolet transparent fluoropolymer films having a thickness and optical absorption that allows at least 20% transmission to the ultraviolet radiation normal to the film surface. In one embodiment, the set of ultraviolet radiation sources 14 can include a set of ultraviolet light emitting diodes. It is understood that the predetermined angular orientation of the set of ultraviolet radiation sources 14 and the predetermined angular distribution of the light emitted from the sources 14 is variable and will depend on factors such as, for example, the shape and size of the electronic device 1 and the particular size and location of the surface areas of the parts of the device that need disinfection, sterilization, sanitization, and the like.

Configuring the set of ultraviolet radiation sources 14 (e.g., ultraviolet light emitting diodes) at an predetermined angular orientation to emit the light 96 to the underlying surface 98 of the electronic device 1 at a predetermined angular orientation via the light guiding layer 94 can be configured to result in a total internal reflection of the light 96. For example, FIG. 14 shows that the light 96 experiences a total internal reflection of light rays 100 from the light guiding layer 94 and the surface 98 of the electronic device 1. The total internal reflection of light rays 100 shown in FIG. 14 further includes a reflection of light rays from a surface 102 of the light guiding layer 94 that forms an interface between the light guiding layer 94 and a low refractive index material 104 such as for example, air, that separates the light guiding structure 92 from an ultraviolet absorbent case or enclosure 18 that can enclose the light guiding structure 92 and the electronic device 1 to prevent the escape of ultraviolet radiation. An internal surface 107 of the ultraviolet absorbent enclosure 18 can be coated with ultraviolet reflective films including, but not limited to, aluminum, polished aluminum, a reflective polymer (e.g., Teflon), a highly ultraviolet reflective expanded polytetrafluoroethylene (ePTFE) membrane (e.g., GORE® Diffuse Reflector Material), and/or the like, to further improve recycling of the ultraviolet radiation in the configuration illustrated in FIG. 14. In this configuration of the set of ultraviolet radiation sources 14 and the light guiding layer 94 as illustrated in FIG. 14, it is possible to attain a total internal reflection at the boundary of the light guiding layer 94 as defined by the surfaces 98 and 102, for at least 50% of the radiation emitted from the set ultraviolet radiation sources 14.

FIG. 15 shows an illustrative ultraviolet radiation system 106 for an electronic device 1 according to another embodiment. In particular, the ultraviolet radiation system 106 uses a combination of various ultraviolet radiation sources in conjunction with at least one sensing device 39 within a light guiding structure 108, such as for example, a partially ultraviolet transparent fluoropolymer, to distribute ultraviolet radiation intensity over a surface of a part or parts of an electronic device in the need of disinfection, sterilization, sanitization and/or the like. In FIG. 15, a set of ultraviolet radiation sources 14A, such as, for example, ultraviolet light emitting diodes, can be used to radiate a surface of a first part 3A of the electronic device 1 and a single ultraviolet radiation source 14B such as, for example, a single ultraviolet light emitting diode can be used to radiate a surface of a second part 3B of the electronic device 1. In one embodiment, the set of ultraviolet radiation sources 14A can be used in a scenario where the surface for the first part 3A of the electronic device 1 is deemed to be highly contaminated, while the single ultraviolet radiation source 14B can be used in a scenario where the surface for the second part 3B of the electronic device 1 is deemed to have a medium contamination.

The sensing device 39 can operate in conjunction with the ultraviolet radiation sources 14A and 14B to determine when a surface of a particular part of the electronic device 1 needs a treatment such as a disinfection, sterilization and or sanitization and/or if already receiving such a treatment, the sensing device can be used to adjust the amount of radiation that is emitted by the sources and directed to the part(s) of the electronic device 1. In one embodiment, the sensing device 39 can include a sensor that can evaluate or monitor the reflectivity of the surface of parts 3A and 3B, provided that the surface can reflect light. For example, the reflectivity can be evaluated with an ultraviolet photodiode. The use of a sensor to evaluate or monitor the reflectivity of the surface of parts 3A and 3B allows the computer system 20 (FIGS. 6 and 7) to control the ultraviolet radiation sources 14A and 14B to increase the amount of radiation, decrease the amount of radiation or stop the radiation based on data provided by the sensor. In an embodiment, a sensor, such as an ultraviolet photodiode, can be configured to monitor transmissivity of the surface of parts 3A and 3B. In this case, the sensor can be installed within the electronic device, behind the surface of the part 3A and 3B.

A touch screen device that can transmit light is one type of electronic device 1 that is suitable for use with the ultraviolet radiation system 106. In such a scenario, the sensing device 39 can determine the least transparent regions of the touch screen device and provide data to the computer system 20 (FIGS. 6 and 7) that can manage the ultraviolet radiation sources 14A and/or 14B to direct ultraviolet radiation to these particular regions of the touch screen. During the irradiation of the particular regions of the touch screen, the sensing device can monitor the reflectivity of the surface or transmissivity of the surface of the region and provide data of the monitoring to the computer system 20 (FIGS. 6 and 7) which determines whether the ultraviolet radiation sources 14A and/or 14B should continue irradiating the region, increase the amount of radiation, decrease the amount of radiation or stop the emission of the radiation from the sources.

In another embodiment, the sensing device 39 can include a touch sensor that collects the location and amount of times that a particular region in the touch screen is touched. In an embodiment, the touch sensor can provide this data to the computer system 20 (FIGS. 6 and 7) which can derive touch statistics based on the amount of times that a particular region of the touch screen is touched. The computer system 20 can then use the touch statistics to determine whether the part of the touch screen needs a treatment such as disinfection, sterilization and/or sanitization. If so, the computer system 20 can then direct the ultraviolet radiation sources 14A and/or 14B to emit radiation to a particular region of the touch screen. In another embodiment, the computer system 20 can use the derived touch statistics to set a schedule for treating the touch screen. For example, if the touch statistics indicate that there is a high amount of usage at a particular location of the touch screen based on the frequency that the location has been touched, then the computer system 20 can direct the ultraviolet radiation sources 14A and/or 14B to increase the intensity of the ultraviolet radiation applied to that area. Similarly, the touch statistics can be used to reduce the intensity of radiation applied to a particular location of the touch screen during a periodic, scheduled treatment set for the touch screen due to the lack of touching at that location.

In another embodiment, the sensing device 39 can include a reflection sensor that detects reflections from a surface of any regions (e.g., 3A and 3B) of the touch screen. The reflection sensor can provide this data to the computer system 20 (FIGS. 6 and 7) which can derive reflection characteristics from the surfaces. The computer system 20 can use these reflection characteristics to correlate with a surface contamination present at any of the various surface parts of the touch screen. The computer system 20 can then use the correlation of reflection characteristics to determine whether the part of the touch screen needs a treatment such as disinfection, sterilization and/or sanitization. If so, the computer system 20 can then direct the ultraviolet radiation sources 14A and/or 14B to emit radiation to a particular region of the touch screen.

The computer system 20 can also use the correlation of reflection characteristics to set a schedule for treating the touch screen. For example, if the correlation of reflection characteristics indicate that there is a high amount of usage at a particular location of the touch screen, then the computer system 20 can direct the ultraviolet radiation sources 14A and/or 14B to increase the intensity of the ultraviolet radiation applied to that area. Similarly, the correlation of reflection characteristics can be used to reduce the intensity of radiation applied to a particular location of the touch screen during a periodic, scheduled treatment set for the touch screen due to the lack of touching at that location.

In another embodiment, the sensing device 39 can include a light sensor that detects light emitted from a surface of any regions (e.g., 3A and 3B) of the touch screen. The light sensor can provide this data to the computer system 20 (FIGS. 6 and 7) which can derive light emission characteristics from the surfaces. The computer system 20 can use these light emission characteristics to correlate with a surface contamination that is present on any of the various surface parts of the touch screen. The computer system 20 can then use the light emission characteristics to determine whether a part of the touch screen needs a treatment such as disinfection, sterilization and/or sanitization. If so, the computer system 20 can then direct the ultraviolet radiation sources 14A and/or 14B to emit radiation to a particular region of the touch screen.

The computer system 20 can also use the light emission characteristics to set a schedule for treating the touch screen. For example, if the light emission characteristics indicate that there is a high amount of contamination present on the touch screen, then the computer system 20 can direct the ultraviolet radiation sources 14A and/or 14B to increase the intensity of the ultraviolet radiation applied to that area. Similarly, the light emission characteristics can be used to reduce the intensity of radiation applied to a particular location of the touch screen during a periodic, scheduled treatment set for the touch screen due to the lack of contamination at that location.

FIGS. 16A-16C show an illustrative ultraviolet radiation system 110 for an electronic device 1 using at least one suction cup 112 with ultraviolet light emitting diodes 114 according to an embodiment. As shown in FIG. 16A, the ultraviolet radiation system 110 illustrates the suction cups 112 with ultraviolet light emitting diodes 114 attached to an ultraviolet absorbent enclosure 18. The ultraviolet absorbent enclosure 18 can also have an ultraviolet light emitting diode 114 integrated within the body of the enclosure. FIG. 16B shows a perspective view of a suction cup 112, while FIG. 16C shows a cross-sectional view of a suction cup 112 with a light emitting diode 114. In operation, the suction cups 112 are configured to adhere to the electronic device 1 upon having a sufficient amount of pressure applied from the ultraviolent absorbent enclosure 18 onto electronic device 1. This causes a negative fluid pressure of air to develop between the electronic device 1 and the suction cups 112. This creates a partial vacuum that allows the suction cups 112 to adhere to the electronic device 1. The ultraviolet radiation system 110 can use the ultraviolet light emitting diode 114 to treat specific regions of the electronic device 1 that are in need of a treatment such as disinfection, sterilization, and/or sanitization. FIG. 16C illustrates how light 116 emitted from an ultraviolet light emitting diode 114 can be directed through a body 118 of the suction cup 112. The ultraviolet radiation system 110 can also use the ultraviolet light emitting diode 114 integrated in the ultraviolet absorbent enclosure 18 to treat other surface regions or parts of the electronic device. In this manner, all of the ultraviolet light emitting diodes 114 can be used to generate a sufficient amount of light to a part of the electronic device depending upon the contamination that is present.

In an embodiment, the suction cups 112 can comprise an elastic polymer or rubber that is fitted with an ultraviolet radiation source such as an ultraviolet light emitting diode located within. The internal surfaces of the suction cups 112 can comprise ultraviolet reflective surfaces for improved recycling of ultraviolet radiation from the ultraviolet light emitting diodes 114. It is understood that the entire area of the electronic device 1 can be contacted by one suction cup 112, or that several smaller suction cups 112 can be used to attach the ultraviolet absorbent enclosure 18 to the surface of the device requiring disinfection, sterilization, sanitization and/or the like. Note that not all suction cups 112 on the UV absorbent enclosure 18 configured to attach to the surface of the device need to have an ultraviolet light emitting diode. For example, a suction cup can include a wave guiding structure, which delivers ultraviolet light from another location. Furthermore, it is understood that the use of the suction cups 112 in the embodiment illustrated in FIG. 16A may be useful for electronic devices containing smooth surfaces to which the suction cups can be attached.

The ultraviolet radiation system 110 illustrated is not meant to be limited to the use of suction cups. Those skilled in the art will appreciate that other fastening means that can adhere to an electronic device can be used to implement an ultraviolet radiation system that can treat a part or parts of an electronic device with a disinfection operation, a sterilization operation, a sanitization operation and/or the like. For example, magnets or a static electricity based enclosure can be used to interface ultraviolet radiation sources with an electronic device.

In another embodiment, the invention provides a method of providing a copy of program code, such as the analysis program 30 (FIG. 6), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for disinfecting an electronic device. In this case, the generating can include configuring a computer system, such as the computer system 20 (FIG. 6), to implement a method of disinfecting the electronic device as described herein. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
an ultraviolet absorbent enclosure;
at least one ultraviolet radiation source embedded within the ultraviolet absorbent enclosure, the at least one ultraviolet radiation source configured to generate ultraviolet radiation within the ultraviolet absorbent enclosure;
a set of partially reflective, partially transmitting layers located adjacent to the ultraviolet absorbent enclosure, wherein the set of partially transmitting layers are configured to distribute the ultraviolet radiation over an object; and
a monitoring and control system for managing the ultraviolet radiation by performing a method comprising:
monitoring a plurality of attributes for the object; and
controlling, based on the monitoring, the ultraviolet radiation directed at the object.

2. The system of claim 1, wherein the set of partially reflective, partially transmitting layers physically separate the at least one ultraviolet radiation source and the object.

3. The system of claim 1, further comprising at least one sensor configured to determine a presence of the object.

4. The system of claim 1, wherein the set of partially reflective, partially transmitting layers is configured to deliver ultraviolet radiation towards the object in order to provide a sufficient dose of ultraviolet radiation over a residency time of the object within the enclosure.

5. The system of claim 1, wherein the plurality of attributes includes a presence of biological activity at a surface area of the object, and wherein the controlling comprises directing a higher dose of ultraviolet radiation to the surface area of the object including the presence of biological activity, wherein the higher dose includes at least one of: an increased intensity level or an increased exposure time.

6. The system of claim 1, wherein the controlling comprises at least one of:
turning on the at least one ultraviolet radiation source;
turning off the at least one ultraviolet radiation source; and
determining a time scheduling for the at least one ultraviolet radiation source.

7. The system of claim 1, wherein the ultraviolet absorbent enclosure includes a switch to turn off the ultraviolet radiation when the object is not located within the ultraviolet absorbent enclosure.

8. An apparatus, comprising:
an object;
an ultraviolet absorbent enclosure for containing the object;
at least one ultraviolet radiation source embedded within the ultraviolet absorbent enclosure, the at least one ultraviolet radiation source configured to generate ultraviolet radiation within the ultraviolet absorbent enclosure; and
a set of partially reflective, partially transmitting layers located adjacent to the ultraviolet absorbent enclosure, wherein the set of partially transmitting layers are configured to distribute the ultraviolet radiation over an object; and
a monitoring and control system for managing the ultraviolet radiation by performing a method comprising:
monitoring a plurality of attributes for the object; and
controlling, based on the monitoring, the ultraviolet radiation directed at the object.

9. The apparatus of claim 8, wherein the set of partially reflective, partially transmitting layers physically separate the at least one ultraviolet radiation source and the object.

10. The apparatus of claim 8, further comprising at least one sensor configured to determine a presence of the object.

11. The apparatus of claim 8, wherein the set of partially reflective, partially transmitting layers is configured to deliver ultraviolet radiation towards the object in order to provide a sufficient dose of ultraviolet radiation over a residency time of the object within the enclosure.

12. The apparatus of claim 8, wherein the plurality of attributes includes a presence of biological activity at a surface area of the object, and wherein the controlling comprises directing a higher dose of ultraviolet radiation to the surface area of the object including the presence of biological activity, wherein the higher dose includes at least one of: an increased intensity level or an increased exposure time.

13. The apparatus of claim 8, wherein the controlling comprises at least one of:
turning on the at least one ultraviolet radiation source;
turning off the at least one ultraviolet radiation source; and
determining a time scheduling for the at least one ultraviolet radiation source.

14. The apparatus of claim 8, wherein the ultraviolet absorbent enclosure includes a switch to turn off the ultraviolet radiation when the object is not located within the ultraviolet absorbent enclosure.

15. An apparatus, comprising:
an object;
an ultraviolet absorbent enclosure for containing the object;
at least one ultraviolet radiation source embedded within the ultraviolet absorbent enclosure, the at least one ultraviolet radiation source configured to generate ultraviolet radiation within the ultraviolet absorbent enclosure;
a set of partially reflective, partially transmitting layers located adjacent to the ultraviolet absorbent enclosure, wherein the set of partially transmitting layers are configured to distribute the ultraviolet radiation over an object;
a switch on the ultraviolet absorbent enclosure to turn off the ultraviolet radiation when the object is not located within the ultraviolet absorbent enclosure; and
a monitoring and control system for managing the ultraviolet radiation by performing a method comprising:
monitoring a plurality of attributes for the object; and
controlling, based on the monitoring, the ultraviolet radiation directed at the object.

16. The apparatus of claim 15, wherein the set of partially reflective, partially transmitting layers physically separate the at least one ultraviolet radiation source and the object.

17. The apparatus of claim 15, further comprising at least one sensor configured to determine a presence of the object.

18. The apparatus of claim 15, wherein the set of partially reflective, partially transmitting layers is configured to deliver ultraviolet radiation towards the object in order to provide a sufficient dose of ultraviolet radiation over a residency time of the object within the enclosure.

19. The apparatus of claim 15, wherein the plurality of attributes includes a presence of biological activity at a surface area of the object, and wherein the controlling comprises directing a higher dose of ultraviolet radiation to the surface area of the object including the presence of biological activity, wherein the higher dose includes at least one of: an increased intensity level; or an increased exposure time.

20. The apparatus of claim 15, wherein the controlling comprises at least one of:
turning on the at least one ultraviolet radiation source;
turning off the at least one ultraviolet radiation source; and
determining a time scheduling for the at least one ultraviolet radiation source.

* * * * *